(12) United States Patent
Kang et al.

(10) Patent No.: US 10,357,780 B2
(45) Date of Patent: Jul. 23, 2019

(54) MAGNETIC CAPTURE OF A TARGET FROM A FLUID

(71) Applicant: PRESIDENT AND FELLOWS OF HARVARD COLLEGE, Cambridge, MA (US)

(72) Inventors: Joo Hun Kang, Boston, MA (US); Donald E. Ingber, Boston, MA (US); Michael Super, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/522,686

(22) PCT Filed: Oct. 27, 2015

(86) PCT No.: PCT/US2015/057516
§ 371 (c)(1),
(2) Date: Apr. 27, 2017

(87) PCT Pub. No.: WO2016/077067
PCT Pub. Date: May 19, 2016

(65) Prior Publication Data
US 2017/0333914 A1 Nov. 23, 2017

Related U.S. Application Data

(60) Provisional application No. 62/068,912, filed on Oct. 27, 2014.

(51) Int. Cl.
| | |
|---|---|
| *B03C 1/00* | (2006.01) |
| *C12N 1/20* | (2006.01) |
| *B03C 1/01* | (2006.01) |
| *B03C 1/033* | (2006.01) |
| *B03C 1/28* | (2006.01) |
| *B03C 1/025* | (2006.01) |

(52) U.S. Cl.
CPC ............... *B03C 1/002* (2013.01); *B03C 1/01* (2013.01); *B03C 1/025* (2013.01); *B03C 1/0332* (2013.01); *B03C 1/286* (2013.01); *B03C 1/288* (2013.01); *C12N 1/20* (2013.01); *B03C 2201/18* (2013.01); *B03C 2201/26* (2013.01)

(58) Field of Classification Search
CPC ...................................................... C12N 1/20
See application file for complete search history.

(56) References Cited

U.S. PATENT DOCUMENTS

| | | |
|---|---|---|
| 2004/0018611 A1 | 1/2004 | Ward et al. |
| 2004/0229212 A1 | 11/2004 | Thiel et al. |
| 2007/0031819 A1 | 2/2007 | Koschwanez et al. |
| 2007/0184463 A1 | 8/2007 | Molho et al. |
| 2008/0014576 A1 | 1/2008 | Jovanovich et al. |
| 2008/0056949 A1 | 3/2008 | Lee et al. |
| 2008/0108120 A1 | 5/2008 | Cho et al. |
| 2008/0113402 A1 | 5/2008 | McMillian |
| 2009/0007861 A1 | 1/2009 | Major |
| 2009/0220932 A1 | 9/2009 | Ingber et al. |
| 2010/0044232 A1 | 2/2010 | Lin et al. |
| 2010/0248214 A1 | 9/2010 | Kshirsagar et al. |
| 2010/0323342 A1 | 12/2010 | Gonzalez Gomez et al. |

FOREIGN PATENT DOCUMENTS

| | | |
|---|---|---|
| WO | 00/64578 A1 | 11/2000 |
| WO | 2007/044642 A2 | 4/2007 |
| WO | 2011/090954 A2 | 7/2011 |
| WO | 2011/091037 A2 | 7/2011 |
| WO | 2012/135834 A2 | 10/2012 |
| WO | 2013/012924 A2 | 1/2013 |
| WO | 2013/126774 A2 | 8/2013 |
| WO | 2013/130875 A1 | 9/2013 |

OTHER PUBLICATIONS

Adams et al. PNAS, 2008, 105(47):18165-18170.*
Kang et al. Nature Medicine, 2014, 20:1211-1216.*
Cooper et al. Lab Chip, 2014, 14:182-188.*
Kang et al., "Magnetophoretic Continuous Purification of Single-Walled Carbon Nanotubes from Catalytic Impurities in a Microfluidic Device", Small 3(10):1784-1791 (2007).
Miltenyi et al., "High Gradient Magnetic Cell Separation With MACS", Cytometry 11:231-238 (1990).
Xia et al., "Combined microfluidic-micromagnetic separation of living cells in continuous flow", Biomedical Microdevices 8:299-308 (2006).

* cited by examiner

*Primary Examiner* — Bin Shen
(74) *Attorney, Agent, or Firm* — Nixon Peabody LLP

(57) ABSTRACT

Disclosed herein is an improved method for magnetic capture of target molecules (e.g., microbes) in a fluid. Kits and solid substrates for carrying the method described herein are also provided. In some embodiments, the methods, kits, and solid substrates described herein are optimized for separation and/or detection of microbes and microbe-associated molecular pattern (MAMP) (including, e.g., but not limited to, a cell component of microbes, lipopolysaccharides (LPS), and/or endotoxin).

12 Claims, 10 Drawing Sheets
Specification includes a Sequence Listing.

*Fig. 4*

| 6-Aug | T0 | T2 | | T4 | | T5 |
|---|---|---|---|---|---|---|
| | | 500uL | 250uL | 500uL | 250uL | 250uL |
| Control | X | O | X | X | O | X |
| SOC | X | O | O | O | O | O |

| 7-Aug | T0 | T2 | | T4 | | T5 |
|---|---|---|---|---|---|---|
| | | 500uL | 250uL | 500uL | 250uL | 250uL |
| Control | X | X | O | O | X | X |
| SOC | X | O | O | O | X | O |

| 13-Aug | T0 | T2 | | T4 | | T5 |
|---|---|---|---|---|---|---|
| | | 500uL | 250uL | 500uL | 250uL | 250uL |
| Control | X | X | O | X | O | X |
| SOC | X | O | O | O | O | O |

| 14-Aug | T0 | T2 | | T4 | | T5 |
|---|---|---|---|---|---|---|
| | | 500uL | 250uL | 500uL | 250uL | 250uL |
| Control | X | X | O | X | X | X |
| SOC | X | O | O | O | O | O |

MAGNETIC CAPTURE OF A TARGET FROM A FLUID

CROSS-REFERENCE TO RELATED APPLICATIONS

This Application is a 371 National Phase Entry of International Patent Application No. PCT/US2015/057516 filed on Oct. 27, 2015 which claims benefit under 35 U.S.C. § 119(e) of the U.S. Provisional Application No. 62/068,912 filed Oct. 27, 2014, the contents of both of which are incorporated herein by reference in their entirety.

GOVERNMENT SUPPORT

The invention was made with Government Support under Contract Nos. N66001-11-1-4180 and HR0011-13-C-0025, both awarded by the United States Department of Defense/DARPA. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 26, 2017, is named 002806-082582-US_SL.txt and is 18,045 bytes in size.

TECHNICAL DISCLOSURE

Embodiments of various aspects described herein relate to methods, compositions, and kits for magnetic capture of a target molecule (e.g., cells, microbes, small molecules, chemicals, drugs, proteins, and/or nucleic acids) from a fluid, including bodily fluids such as blood, food, water, and environmental sources.

BACKGROUND

One of the disadvantages of conventional magnetic capture methods is that the magnetic separation is based on relatively weak magnetic field gradients, which in turn provide limited effectiveness, for example, in separating smaller magnetic particles from a fluid (e.g., a solution). For example, the existing magnetic capture methods and systems are generally limited to magnetic beads greater than 1 micrometer in diameter. In addition, the relatively weak magnetic field gradient limits the size of the tube and the volume of fluid that can be processed. For example, DynaMag2™ (Invitrogen, Grand Island, N.Y.) is designed to work with magnetic beads greater than 1 micrometer in diameter and is thus not effective with smaller magnetic beads, such as those in the 50 and 500 nanometer diameter range.

Many methods have been used to generate increased magnetic flux density gradients (Kang et al., Small 3, 1784-1791 (2007); and Xia et al., Biomed Microdevices 8, 299-308 (2006)), for example, using various microelectromechanical system (MEMS) technologies, but they require labor-intensive and time-consuming fabrication processes for structuring ferromagnetic materials at the nanometer to micrometer scale, such as photolithography, LIGA (Lithographie-Galvanoformung-Abformung/Lithography-Electroplating-Molding), and CMP (chemical mechanical polishing). The MACS magnetic column (Miltenyi®) (Miltenyi et al., Cytometry 11, 231-238 (1990)) can be used to trap smaller (e.g., 50 nm) magnetic particles. However, the MACS systems use steel wool and/or magnetizable wires packed into a column to accomplish magnetic gradient enhancement. However, the use of steel wool and/or magnetizable wires in a column makes the system harder to wash captured cells, prone to clogging, and/or prone to inducing clotting when used with blood. In addition, the throughput of the MACS systems is very limited (0.5 mL per a column). Due to the confined structures of the steel wool, it is difficult to apply the system to various experimental conditions or sample containers, such as tube or well plate configurations, fluidic devices (including microfluidic devices), etc. Accordingly, there is a need to develop novel and versatile methods, kits, devices, and systems for efficient and/or high throughput magnetic separation and/or capture of at least one or more target molecules from a fluid or solution.

SUMMARY

While smaller magnetic particles are more efficient in binding a wider range of target molecules, efficient removal of small magnetic particles from a fluid is challenging due to their low magnetic moments. Aspects described herein stem from, at least in part, discovery that forming a 2D or 3D micro- or nano-structure of magnetic field concentrating particles on a magnetic capture surface or a fluid-contact surface of a magnetic separation chamber, prior to introducing a fluid sample (comprising magnetic particles, e.g., target-binding magnetic particles) into the chamber to undergo magnetic separation, significantly enhances magnetic separation efficiency of the magnetic particles (e.g., target-binding magnetic particles), even when the magnetic moments of the magnetic particles are too low to be removed by the existing magnetic separation methods. During magnetic separation, the magnetic field concentrating particles are magnetized by an externally applied magnetic field, and substantially aligned with magnetic flux lines of the magnetic field to form a 2D or 3D micro- or nano-structure on a magnetic capture surface or a fluid-contact surface of a magnetic separation surface, thereby increasing or concentrating the magnetic field or flux density gradient locally experienced by magnetic particles in a fluid, as compared to the magnetic field or flux density gradient without the magnetic field concentrating particles. Such magnetic separation method can be used to separate or capture at least one or more (e.g., at least two or more) targets from a fluid when magnetic particles are adapted or functionalized to specifically bind the target(s).

In particular, inventors have demonstrated inter alia that the magnetic separation efficiency of microbes (e.g., *S. aureus*) bound to small magnetic beads (e.g., 50 nm or 128 nm in diameter) increased significantly from 15%-30% to at least 95% or higher, when the fluid-contact surface of a microfluidic device channel was dispersed with ferromagnetic particles forming a 2D or 3D micro- or nano-ferromagnetic structure thereon, prior to introducing a fluid to be cleansed for magnetic separation. Additionally, the inventors have used such method to effectively remove pathogenic contaminants from cord blood.

The concept of forming a 2D or 3D micro- or nano-structure of magnetic field concentrating particles on a fluid-contact surface can be extended to magnetic separation of any target using appropriate target-binding magnetic particles in a wide range of separation device formats, e.g., for static or continuous flow. Thus, the inventors have developed a novel, versatile and cost-effective method for increasing the magnetic flux density gradient in a magnetic particle-based separation device of any format (e.g., tube, multi-well plate, and/or microfluidic channels), and hence improving magnetic separation efficiency of a target molecule from a fluid. Accordingly, aspects described herein relate to methods, kits, devices, and compositions for sensitive magnetic separation or capture of at least one or a plurality of (e.g., at least two or more) target molecules from a fluid. The methods, kits, devices, and compositions described herein can be used for various applications including cleansing biological fluids as well as food, water, culture medium (e.g., for pharmaceutical manufacturing or brewing), or any other liquid.

One aspect described herein relates to a method of separating magnetic particles from a fluid. The method comprises: (a) subjecting a magnetic capture surface and magnetic field gradient concentrating particles to a magnetic field gradient (a gradient of a magnetic field), wherein the magnetic field gradient concentrating particles, in the presence of the magnetic field gradient, distribute on at least a portion of a magnetic capture surface and substantially align along magnetic flux lines of the magnetic field; and (b) contacting the magnetic capture surface with a fluid comprising magnetic particles, wherein the magnetic field gradient concentrating particles act as local magnetic field gradient concentrators. At least a portion of the magnetic particles are attracted to the magnetic field gradient concentrating particles in the presence of the magnetic field gradient, thereby separating the magnetic particles from the fluid. Due to enhancement of the magnetic field gradient by magnetic field gradient concentrating particles substantially aligning along with magnetic flux lines of a magnetic field applied to the method, such method is particularly useful for separation of small magnetic particles with a magnetic moment that is too low to be removed by the existing magnetic separation methods.

When the magnetic particles are functionalized to specifically bind a target, the target-binding magnetic particles can be added to a fluid for capture or separation of the target, if present, from the fluid. Accordingly, another aspect described herein relates to a method of capturing, removing, or separating one or more (e.g., at least two or more) targets from a fluid. The method comprises introducing a fluid and target-binding magnetic particles to a magnetic separation chamber in the presence of a magnetic field gradient (a gradient of a magnetic field), wherein at least a portion of a fluid-contact surface of the magnetic separation chamber comprises magnetic field gradient concentrating particles distributed thereon and substantially aligned along magnetic flux lines of the magnetic field. The magnetic field gradient concentrating particles act as local magnetic field gradient concentrators, thus attracting at least a portion (e.g., at least 70% or more) of the target-binding magnetic particles to the magnetic field gradient concentrating particles in the presence of the magnetic field gradient. Target(s) bound on the target-binding magnetic particles can then be captured, removed, or separated from the fluid.

In some embodiments of this aspect and other aspects described herein, the target-binding magnetic particles can be added to the fluid, prior to introducing the mixture to the magnetic separation chamber, in which a magnetic field gradient can be applied. Thus, the target(s) are allowed to bind to the target-binding magnetic particles, prior to exposing the mixture to a magnetic field gradient.

In some embodiments of this aspect and other aspects described herein, the fluid or fluid sample and the target-binding magnetic particles can be added to a sample chamber or an open-top magnetic separation chamber without any magnetic field gradient therein. A structure comprising a fluid-contact magnetic capture surface and magnetic field gradient concentrating particles distributed on thereon can then be introduced into the sample chamber or the open-top magnetic separation chamber so that the fluid-contact magnetic capture surface is contacted with the mixture comprising the fluid and the target-binding magnetic particles contained in the sample chamber. The magnetic field gradient concentrating particles distributed on the fluid-contact magnetic capture surface are substantially aligned along magnetic flux lines of a magnetic field (e.g., generated within the structure or applied externally to the structure).

In some embodiments of this aspect and other aspects described herein, the magnetic field gradient concentrating particles form magnetic micro- or nano-structures on at least a portion of the fluid-contact surface of the magnetic separation chamber. The magnetic micro or nano-structures can be two dimensional or three dimensional.

In some embodiments of this aspect and other aspects described herein, at least 50% area or higher of the fluid-contact surface comprises the magnetic field gradient concentrating particles distributed thereon.

In some embodiments of this aspect and other aspects described herein, the magnetic field gradient concentrating particles can comprise superparamagnetic particles, paramagnetic particles, ferrimagnetic particles, ferromagnetic particles, or combinations thereof. In one embodiment, the magnetic field gradient concentrating particles are ferromagnetic particles. In one embodiment, ferromagnetic particles are particles of reduced iron, atomized iron, electrolyte iron, or combinations thereof.

In some embodiments of this aspect and other aspects described herein, the magnetic field gradient concentrating particles by themselves are not able to bind or capture a target. In some embodiments of this aspect and other aspects described herein, the magnetic field gradient concentrating particles do not comprise metal oxide (e.g., iron oxide). In some embodiments, the magnetic field gradient concentrating particles can be treated to reduce non-specific interaction with a target to be removed or separated from a fluid, e.g., by coating the surface of the magnetic field gradient concentrating particles with a blocking agent. Non-limiting examples of a blocking agent include a lubricant (e.g., but not limited to silicone and/or mold-release agent), a polymer (e.g., but not limited to silicon-based polymer such as polydimethylsiloxane (PDMS)), milk proteins, bovine serum albumin, blood serum, whole blood, and a combination of two or more thereof.

The magnetic field gradient concentrating particles can be larger, comparable to, or smaller than the target-binding magnetic particles in size. In some embodiments of this aspect and other aspects described herein, the diameter of the magnetic field gradient concentrating particles ranges from about 50 nm to about 5 mm. In one embodiment, the diameter of the magnetic field gradient concentrating particles is about 300 µm.

The methods of various aspects described herein can be applied to magnetic particles (e.g., target-binding magnetic particles) of various materials and/or sizes, including magnetic particles with weak magnetic moments or small magnetic particles (e.g., nanoparticles). In some embodiments, the magnetic particles (e.g., target-binding magnetic particles) are particles of paramagnetic and/or superparamagnetic materials. In one embodiment, the magnetic particles (e.g., target-binding magnetic particles) are used in the methods described herein. In some embodiments, the diameter of the magnetic particles (e.g., target-binding magnetic particles) is no more than 250 nm, no more than 100 nm, no more than 50 nm, or no more than 5 nm.

The magnetic field gradient concentrating particles locally increase magnetic flux density gradient when they are exposed to a magnetic field. Thus, the methods described herein increase the efficiency of removing magnetic particles from a fluid and thereby increasing the efficiency of magnetically capturing one or more target(s) from the fluid that is bound on targeting-binding magnetic particles. The increase in the efficiency can be at least about 50% (including, e.g., at least about 60%, at least about 70%, at least about 80%, at least about 90%) or more, as compared to the efficiency in the absence of the magnetic field concentrating particles. In some embodiments, the efficiency of magnetically capturing the target-bound targeting-binding magnetic particles from the fluid can be increased by at least about 1.1-fold (including, e.g., at least about 1.5-fold, at least about 2-fold, at least about 3-fold, at least about 4-fold) or more, as compared to the efficiency in the absence of the magnetic field concentrating particles.

The methods of various aspects described herein can be amenable to a wide range of magnetic separation devices in various configurations. Thus, the magnetic separation chamber can comprise a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a hollow fiber, or any combinations thereof. In some embodiments, the method described herein can be used in non-fluidic devices (e.g., any sample carriers such as tubes with one open end, and multi-well plates). Alternatively, the method described herein can be used in a fluidic device that allows a fluid flowing therethrough. In this embodiment, the fluid can flow through the magnetic separation chamber at a flow rate of about 1 ml/hr to about 10 L/hr.

Fluids of any sources can be introduced into the magnetic separation chamber. For example, the fluid can be a biological fluid obtained or derived from a subject, a fluid or specimen obtained from an environmental source, a fluid from a cell culture, a microbe colony, or any combinations thereof. In one embodiment, the fluid is a biological fluid selected from blood, plasma, cord blood, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof. In one embodiment, the fluid is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, beer brewing, or any combinations thereof.

Methods and compositions for forming target-binding magnetic particles are known in the art. In some embodiments, target-binding molecules can be attached to magnetic particles via at least one or more linkers described herein. In one embodiment, the linker is a peptidyl linker. An exemplary peptidyl linker is an immunoglobulin or a portion thereof (e.g., but not limited to an Fc portion of an immunoglobulin).

The target-binding magnetic particles are magnetic particles adapted to specifically bind a target molecule of interest. Example target molecules that can be captured or removed from a fluid include, without limitation, cells, proteins, nucleic acids, microbes, small molecules, chemicals, toxins, drugs, and combinations thereof.

In one embodiment, the target-binding magnetic particles are adapted to specifically bind a microbe (referred to as "microbe-binding magnetic particles"). The microbe-binding magnetic particles comprise on their surface microbe-binding molecules. Exemplary microbe-binding molecule for use in the microbe-binding magnetic particles are opsonins, lectins, antibodies and antigen binding fragments thereof, proteins, peptides, peptidomimetics, carbohydrate-binding proteins, nucleic acids, carbohydrates, lipids, steroids, hormones, lipid-binding molecules, cofactors, nucleosides, nucleotides, nucleic acids, peptidoglycan, lipopolysaccharide-binding proteins, small molecules, and any combination thereof.

In some embodiments, the microbe-binding molecule comprises at least a microbial-binding portion of C-type lectins, collectins, ficolins, receptor-based lectins, lectins from the shrimp *Marsupenaeus japonicas*, non-C-type lectins, lipopolysaccharide (LPS)-binding proteins, endotoxin-binding proteins, peptidoglycan-binding proteins, or any combinations thereof. In some embodiments, the microbe-binding molecules is selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), or any combinations thereof.

In some embodiments, the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.

In some embodiments, the microbe-binding molecule comprises an amino acid sequence selected from the group consisting of: SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and any combinations thereof.

Another aspect described herein relates to a kit comprising (i) a device comprising a magnetic separation chamber or a magnetic capture surface; (ii) one or more containers containing magnetic field gradient concentrating particles; and (iii) one or more containers containing target-binding magnetic particles.

In some embodiments, the device can further comprise a structure or module that can produce a magnetic field. In some embodiments the structure or module that can produce a magnetic field can be detachable from the device, e.g., the magnetic separation chamber or magnetic capture surface.

The device comprising a magnetic separation chamber or a magnetic capture surface can be any fluid container or fluid processing device. For example, the device can be an eppendorf tube, a multi-well plate, a flask (e.g., a tissue culture flask), an extracorporeal device, a mixer, a hollow fiber cartridge, a microfluidic device, or any combinations thereof. In some embodiments, the device is a microfluidic device. In one embodiment, the device can be an organ-on-chip device (e.g., a biospleen device).

A solid substrate comprising a surface having magnetic field gradient concentrating particles distributed thereon and substantially aligned along magnetic flux lines of a magnetic field is also described herein. The solid substrate further comprises a target-binding magnetic particle and a target.

In some embodiments, the solid substrate can further comprise a structure or device that produces a magnetic field. Thus, the magnetic field gradient concentrating particles can be substantially aligned along magnetic flux lines of the magnetic field produced by the structure or device.

In one embodiment, the target is bound to the target-binding magnetic particle.

In some embodiments, the solid substrate is selected from the group consisting of a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a microfluidic device, a hollow fiber, or any combinations thereof.

BRIEF DESCRIPTION OF THE DRAWINGS

FIG. 1A shows a diagrammatic scheme of an example ferromagnetic particle-integrated microfluidic device (e.g., biospleen device). To create such a device, ferromagnetic particles suspended in buffer are trapped in the channel by pumping the solution through the device with permanent magnets attached. While one permanent magnet on one side of the device can be used, placing permanent magnets on both sides of the device significantly increased the magnetic flux density gradients around the ferromagnetic particles trapped in the channel. FIG. 1B shows a view of an example microfluidic device (e.g., biospleen device) without ferromagnetic particles. The biospleen device is a microfluidic device 100 that comprises two adjacent channels (source channel 140 and collection channel 150) that are connected to each other by a series of transfer channels 160: the source channel 140 contains flowing fluid to be cleansed, e.g., blood, and the collection channel 150 has a buffered solution that collects and removes the target molecules that travel through the transfer channels 160. In one embodiment, the device 100 comprises a central body 110 and outer layers 120 and 130. A fluid or fluid sample can flow into the source channel 140 through one or more inlet ports 142 and exits the device 100 through one or more outlet ports 144. A collection fluid can flow into the collection channel 150 through one or more inlet ports 152 and exits the device 100 through one or more outlet ports 154. See the International Patent Application No. WO 2012/135834, the content of which is incorporated herein by reference in its entirety, for additional description of the biospleen device. Other microfluidic devices of different designs can also be employed. FIG. 1C shows a cross-sectional view of the device in FIG. 1B that is used in combination with ferromagnetic particles to enhance magnetic separation efficiency. In one embodiment, the device 100 comprises a source channel 140, a collection channel 150, and a plurality of transfer channels 160 connecting the source channel 140 and the collection channel 150. While the transfer channels 160 are shown oriented substantially perpendicular to the source channel 140 and collection channel 150, the transfer channels 160 can be oriented in a range of angles (e.g., 1 to 90 degrees, where 0 degrees corresponds to the direction of flow in the source channels 140) with respect to the source channel 140. One or more magnetic sources 410, such as a magnet, can be positioned in close proximity to the collection channel 150. When a magnetic source 410 is positioned closer to a fluid-contact surface 151 of the collection channel 150, ferromagnetic particles 170 are distributed on the fluid-contact surface 151 of the collection channel 150. FIG. 1D shows a cross-sectional view of the device 100 in FIG. 1B with two magnetic sources 410 (e.g., magnets) placed facing each other, where a magnetic source 410 (e.g., a magnet) is placed in closer proximity to the collection channel 150 and another magnetic source 410 (e.g., another magnet) is placed in closer proximity to the source channel 140 (left panel), and a schematic diagram showing distribution of magnetic flux lines generated by the two magnets (right panel). In FIG. 1D, the ferromagnetic particles substantially align along the magnetic flux lines. FIG. 1E is a photograph of a ferrofluid in a magnetic field showing normal-field instability caused by a magnet placed beneath a dish. A ferrofluid is a colloidal liquid comprising nanoscale ferromagnetic, or ferrimagnetic, particles suspended in a carrier fluid (usually an organic solvent or water). FIG. 1F is a photograph showing an example distribution of magnetic flux lines based on one embodiment of magnet arrangement. FIG. 1G is a schematic diagram showing various sizes of ferromagnetic particles (e.g., nano- or micro-sized ferromagnetic particles) aggregating and aligning along magnetic flux lines. In some embodiments, smaller ferromagnetic particles can preferentially aggregate and align along magnetic flux lines at a higher magnetic flux density. In some embodiments, larger ferromagnetic particles can preferentially aggregate and align along magnetic flux lines at a lower magnetic flux density. Accordingly, in some embodiments of various aspects described herein, the magnetic field gradient concentrating particles utilized in the methods described herein can comprise a mixture of different sized magnetic field gradient concentrating particles. A mixture of different sized magnetic field gradient concentrating particles can be used when the magnetic field gradient is not uniform.

FIG. 4 is a table showing the results of blood culture vials inoculated with cord blood samples (250 uL) that has been treated in a ferromagnetic particles-integrated microfluidic device (e.g., biospleen device) for an indicated time period (T0=0 hour; T2=2 hours; T4=4 hours; and T5=5 hours). The microbe removal efficiency was determined based on the turbidity of the inoculated blood culture vials after a 5-day culture at 37° C. The "O" symbol indicates the 250 μL cord blood sample did not contain pathogen while the "X" symbol indicates that the 250 μL cord blood sample contained at least one pathogen.

FIG. 6A shows the cross-sectional view of the KingFisher deep well plate working with bar magnets and ferromagnetic particles. Integration of ferromagnetic particles with the KingFisher system enhances magnetic capturing efficiency even when 50 nm magnetic beads were used to capture target species, e.g., microbes such as pathogens. FIG. 6B shows that the ferromagnetic particle-integrated 96 well plates can capture and significantly deplete 50 nm magnetic beads when combined with a magnetic plate holder and a shaker. FIG. 6C shows another embodiment of a ferromagnetic particle-integrated 96-well plate system. A multiwell plate (e.g., 96 well plate) with ferromagnetic particles added in each well is brought in close proximity to or in contact with an array of magnets. During magnetic separation, the multiwell plate can be rotated to facilitate the mixing. The system can be used to pull down 50 nm magnetic beads (e.g., bound with target species such as pathogens) efficiently. FIG. 6D is a bar graph comparing the depletion efficiency of RS218 *E. coli* bound on 50 nm microbe-binding magnetic particles (e.g., FcMBL-coated magnetic beads) in different 96-well plate-based platform (in shown in FIGS. 6A-6C) using ferromagnetic particles. The conventional method without ferromagnetic particles was also performed as a control. All three different capture platforms yielded over 90% depletion efficiency of 50 nm bead bound RS218 *E. coli*.

DETAILED DESCRIPTION OF THE INVENTION

Figure 1A:
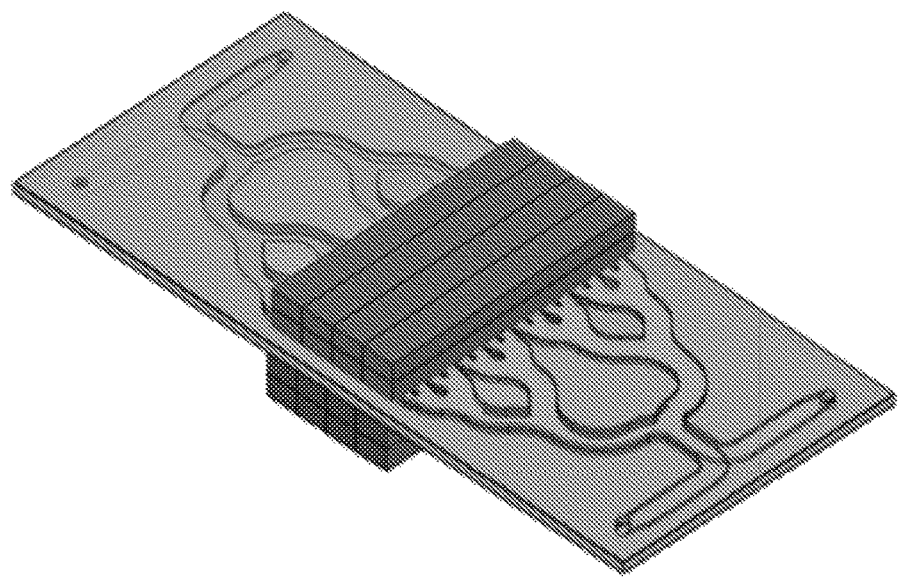
FIGS. 1A-1G show diagrammatic views of ferromagnetic particle-integrated devices according to various embodiments described herein. The device was used in the experiments described in the Examples herein to remove microbes or microbe-associated molecular patterns (MAMP) from a fluid.
Figure 1B:
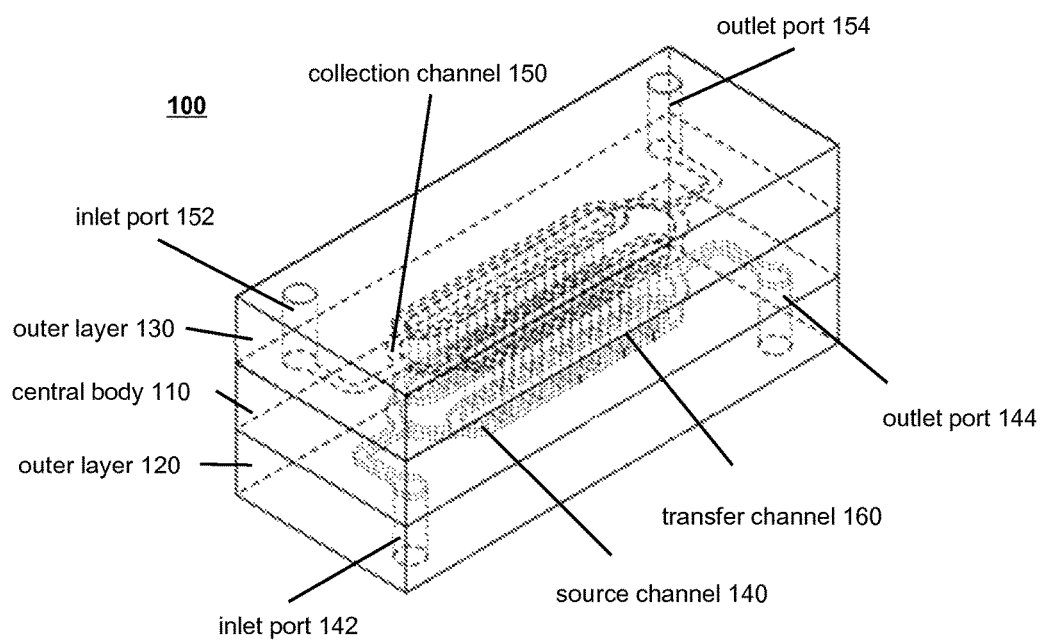
Figure 1C:
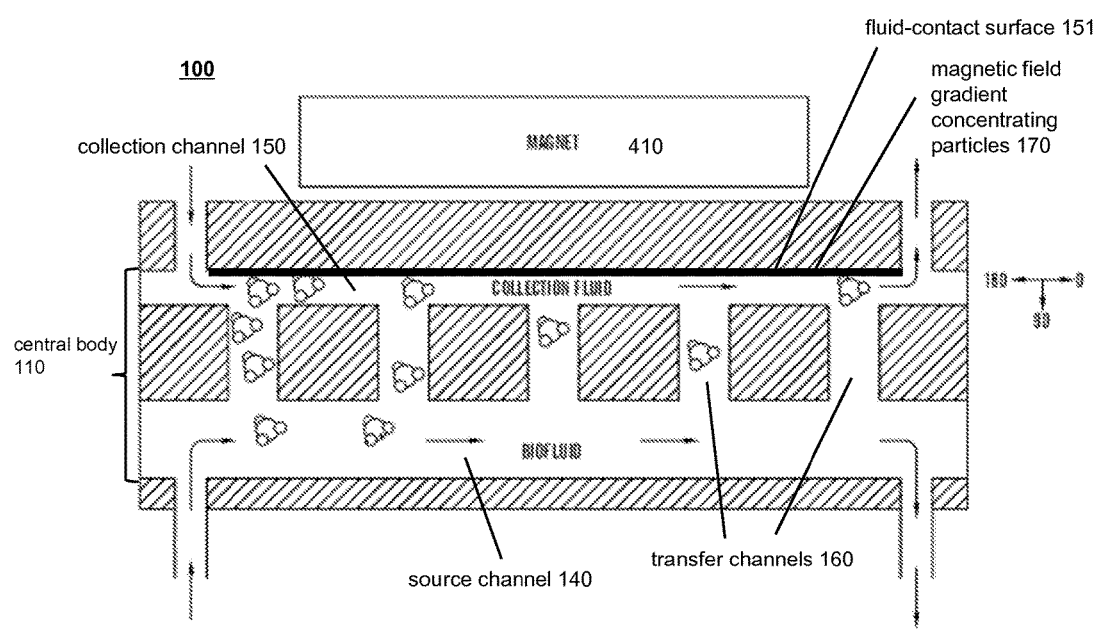

While smaller magnetic particles are more efficient in binding a wider range of target molecules, methods for effective removal of small magnetic particles from a fluid are lacking due to their low magnetic moments. Aspects described herein stem from, at least in part, discovery that forming a 2D or 3D micro- or nano-structure of magnetic field concentrating particles on a magnetic capture surface or a fluid-contact surface of a magnetic separation chamber, prior to introducing a fluid sample (comprising magnetic particles, e.g., target-binding magnetic particles) into the chamber to undergo magnetic separation, significantly enhances magnetic separation efficiency of the magnetic particles (e.g., target-binding magnetic particles). When a magnetic field gradient is applied across a magnetic capture surface or magnetic separation chamber, the presence of a 2D or 3D micro- or nano-structure of the magnetic field concentrating particle increases or concentrates the local magnetic flux density gradient that is experienced by magnetic particles (e.g., target-binding magnetic particles) in a fluid. Thus, magnetic particles (e.g., target-binding magnetic particles) are more readily attracted to the magnetic field concentrating particles in the presence of a magnetic field gradient, even when the magnetic moments of the target-binding magnetic particles are too low to be removed by the existing magnetic separation methods. In particular, the inventors have demonstrated inter alia that the magnetic separation efficiency of microbes (e.g., *S. aureus*) bound to small magnetic beads (e.g., 50 nm or 128 nm in diameter) increased significantly from 15%-30% to at least 95% or higher, when the fluid-contact surface of a microfluidic device channel was dispersed with ferromagnetic particles forming a 2D or 3D micro- or nano-ferromagnetic structure thereon, prior to introducing a fluid to be cleansed for magnetic separation. Additionally, the inventors have used such method to effectively remove pathogenic contaminants from cord blood.

While the inventors demonstrated the magnetic separation efficiency of removing target species (e.g., microbes) from a fluid in a channel, e.g., of a microfluidic device, the concept of forming a 2D or 3D micro- or nano-structure of magnetic field concentrating particles on a fluid-contact surface can be extended to magnetic separation of any target species using appropriate target-binding magnetic particles in a wide range of separation device formats, e.g., non-fluidic and fluidic devices or systems. Thus, the inventors have developed a novel, versatile and cost-effective method for increasing the magnetic flux density gradient in a magnetic particle-based separation device of any format (e.g., tube, multi-well plate, and/or microfluidic channels), and hence improving magnetic separation efficiency of a target molecule from a fluid. Accordingly, aspects described herein relate to methods, kits, devices, and compositions for sensitive magnetic separation or capture of at least one or a plurality of (e.g., at least two or more) target molecules from a fluid. The methods, kits, devices, and compositions described herein can be used for various applications including cleansing biological fluids as well as food, water, culture medium (e.g., for pharmaceutical manufacturing or brewing), or any other liquid that can be introduced through a fluidic device.

Methods of Capturing, Separating, or Removing a Magnetic Particle and/or a Target Molecule from a Fluid One aspect described herein relates to a method of separating magnetic particles from a fluid. The method comprises: (a) subjecting a magnetic capture surface and magnetic field gradient concentrating particles to a magnetic field gradient (a gradient of a magnetic field), wherein the magnetic field gradient concentrating particles, in the presence of the magnetic field gradient, distribute on at least a portion of a magnetic capture surface and substantially align along magnetic flux lines of the magnetic field; and (b) contacting the magnetic capture surface with a fluid comprising magnetic particles, wherein the magnetic field gradient concentrating particles act as local magnetic field gradient concentrators. At least a portion of the magnetic particles are attracted to the magnetic field gradient concentrating particles in the presence of the magnetic field gradient, thereby separating the magnetic particles from the fluid. Due to enhancement of the magnetic field gradient by magnetic field gradient concentrating particles substantially aligning along with magnetic flux lines of a magnetic field applied to the method, such method is particularly useful for separation of small magnetic particles with a magnetic moment that is too low to be removed by the existing magnetic separation methods.

Figure 6A:
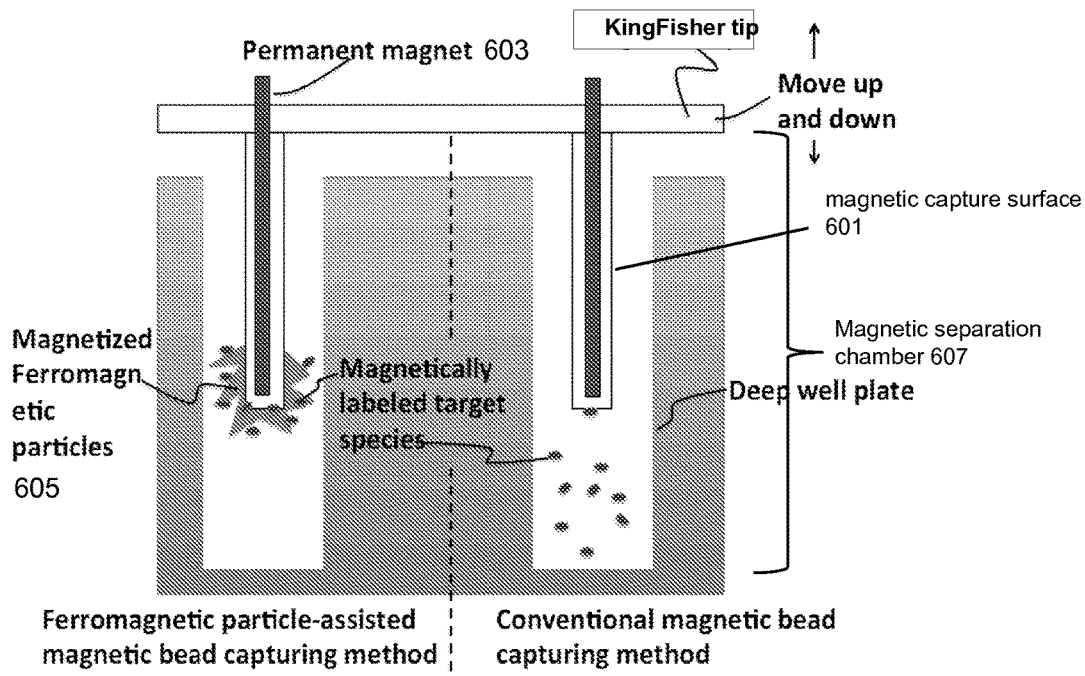
FIGS. 6A-6D show application of the methods described herein in various multi-well ELISA platform (e.g., 96-well plate-based ELISA platform).

As used herein, the term "magnetic capture surface" refers to a fluid-contact surface that can provide or generate a magnetic field gradient, and/or that can be exposed to a magnetic field gradient during operation of magnetic separation. The magnetic capture surface can form part of a magnetic separation chamber. In some embodiments, the magnetic capture surface can be integral to the magnetic separation chamber. For example, the magnetic capture surface can be a surface of a channel (e.g., in a microfluidic device), or a surface of a microwell (e.g., in a multi-well plate). In some embodiments, the magnetic capture surface can be detachable from the magnetic separation chamber. For example, as shown in FIG. 6A, the magnetic capture surface 601 is exposed to a magnetic field gradient (e.g., generated by a magnet 603), and magnetic field gradient concentrating particles (e.g., ferromagnetic particles) 605 are attracted to the magnetic capture surface 601 in the presence of the magnetic field gradient and deposit (e.g., as a layer or an aggregate structure) on at least a portion of the magnetic capture surface 601. The composite structure comprising the magnetic capture surface 601 and the magnetic field gradient concentrating particles (e.g., ferromagnetic particles) can then be brought into contact with a fluid sample contained in a sample chamber, thereby forming a magnetic separation chamber 607. Inside the magnetic separation chamber 607, magnetic particles (e.g., target-binding magnetic particles) present in the fluid sample experience a magnetic force due to the magnetic field gradient enhanced locally by the magnetic field gradient concentrating particles 605 and are attracted and bound to the magnetic field gradient concentrating particles 605. Thus, the magnetic particles (e.g., target-binding magnetic particles) are separated from the fluid sample.

Due to enhancement of local magnetic field gradients by the presence of magnetic field gradient concentrating particles aligning along with magnetic flux lines of an applied magnetic field, such technique is particularly useful for separation of small magnetic particles with a magnetic moment that is too low to be removed by the existing magnetic separation methods.

When the magnetic particles are functionalized to specifically bind a target (e.g., the surface of a magnetic particle is functionalized or coated with a target-binding molecule on its), the functionalized magnetic particles (also referred to herein as "target-binding magnetic particles" can be added to a fluid sample for capture or separation of a target species, if present, from the fluid. Accordingly, in another aspect, described herein is a method of capturing, removing, or separating a target molecule or species from a fluid or a fluid sample based on magnetic field gradient concentrating particles dispersed or distributed on a fluid-contact magnetic capture surface to enhance magnetic separation strength. The method comprises: introducing a fluid and target-binding magnetic particles to a magnetic separation chamber comprising a magnetic field gradient (a gradient of a magnetic field) therein, wherein at least a portion of a fluid-contact surface of the magnetic separation chamber comprises magnetic field gradient concentrating particles distributed on the fluid-contact surface. At least a portion of the target-binding magnetic particles are attracted to the magnetic field gradient concentrating particles in the presence of the magnetic field gradient. Thus, a target bound on the target-binding magnetic particles is captured, removed, or separated from the fluid.

In some embodiments of this aspect and other aspects described herein, the target-binding magnetic particles can be added to the fluid or fluid sample, prior to introducing the mixture to the magnetic separation chamber comprising a magnetic field gradient therein. Thus, the target(s) are allowed to bind to the target-binding magnetic particles, prior to exposing the mixture to a magnetic field gradient for magnetic separation.

In some embodiments of this aspect and other aspects described herein, the fluid or fluid sample and the target-binding magnetic particles can be added to a sample chamber or an open-top magnetic separation chamber without any magnetic field gradient therein. A structure comprising a fluid-contact magnetic capture surface and magnetic field gradient concentrating particles distributed on thereon can then be introduced into the sample chamber or the open-top magnetic separation chamber so that the fluid-contact magnetic capture surface is contacted with the mixture comprising the fluid and the target-binding magnetic particles contained in the sample chamber. The magnetic field gradient concentrating particles distributed on the fluid-contact magnetic capture surface are substantially aligned along magnetic flux lines of a magnetic field (e.g., generated within the structure or applied externally to the structure).

In some embodiments of this aspect and other aspects described herein, at least 70% or more (including, e.g., at least 80%, at least 90%, at least 95%, at least 97%, or more) of the target-binding magnetic particles in a fluid or fluid sample can be captured, separated, or removed from the fluid or fluid sample.

As used herein, the term "fluid-contact surface" refers to a surface or portion thereof that will be in contact with a fluid upon introduction of the fluid. In some embodiments, the fluid-contact surface is also subjected to exposure of a magnetic field gradient for attracting target-binding magnetic particles to bind thereon. In some embodiments, the term "fluid-contract surface" also encompasses a magnetic capture surface.

As used interchangeably herein, the terms "a magnetic field gradient" and "a gradient of a magnetic field" refer to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions. The magnetic field gradient can be static or transient. In some embodiments, the magnetic field gradient can be uniform. In some embodiments, the magnetic field gradient can be non-uniform. The magnetic field gradient can be generated across a magnetic capture surface or inside a magnetic separation chamber by any methods known in the art, e.g., using a magnet, such as a permanent magnet.

In some embodiments of this aspect and other aspects described herein, at least 5% area or more of the fluid-contact surface or magnetic capture surface (that is exposed to a magnetic field gradient) comprises the magnetic field gradient concentrating particles distributed thereon. In general, the magnetic separation efficiency increases with larger area coverage of the fluid-contact surface or magnetic capture surface by the magnetic field gradient concentrating particles. Thus, in some embodiments, at least 10% area, at least 20%, at least 30%, at least 40%, at least 50%, at least 60%, at least 70%, at least 80%, at least 90%, at least 95% or more of the fluid-contact surface or magnetic capture surface (that is exposed to a magnetic field gradient) comprise the magnetic field gradient concentrating particles distributed thereon. In one embodiment, 100% of the fluid-contact surface or magnetic capture surface (that is exposed to a magnetic field gradient) comprises the magnetic field gradient concentrating particles distributed thereon.

In some embodiments, the magnetic field gradient concentrating particles are distributed on at least a portion of (e.g., at least 5% area or more) the fluid-contact surface or magnetic capture surface to form a layer. The layer can be uniform or uneven in thickness. The layer thickness can vary depending on a number of factors including, e.g., but not limited to design of a magnetic separation chamber, placement and/or manipulation of magnet(s) to distribute magnetic field gradient concentrating particles on a fluid-contact surface, distribution of magnetic flux lines, amount of the magnetic field gradient concentrating particles being distributed on a fluid-contact surface, area of a fluid-contact surface to be covered by magnetic field gradient concentrating particles, and combinations thereof.

To optimize the amount of the magnetic field gradient concentrating particles used in a magnetic separation chamber and/or the layer thickness of the magnetic field gradient concentrating particles, one can determine the magnetic isolation efficiency using different amount of the magnetic field gradient concentrating particles on a fluid-contact surface. The magnetic isolation efficiency can increase with the amount of the magnetic field gradient concentrating particles used, and become plateau beyond a certain point. Thus, in some embodiments, the optimum amount of the magnetic field gradient concentrating particles can correspond to a point at or close to the beginning of the plateau, which reflects the highest magnetic isolation efficiency. In some embodiments, the amount of the magnetic field gradient concentrating particles distributed on a fluid-contact surface or a magnetic capture surface can range from about 0.01 mg/mm$^2$ to about 5 mg/mm$^2$, about 0.025 mg/mm$^2$ to about 3 mg/mm$^2$, or about 0.05 mg/mm$^2$ to about 1 mg/mm$^2$.

Figure 1D:
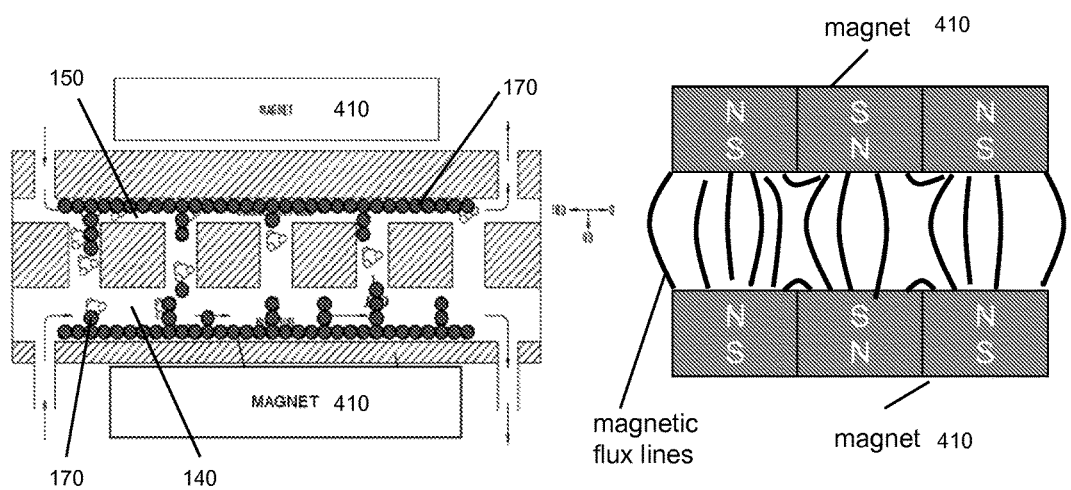
Figure 1E:
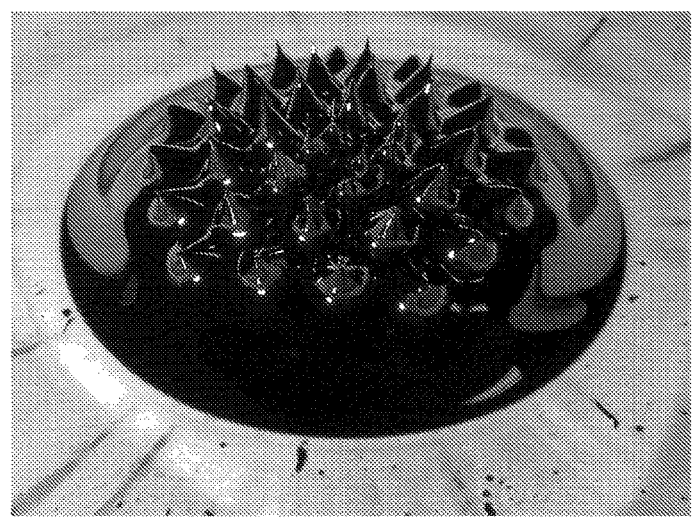
Figure 1F:
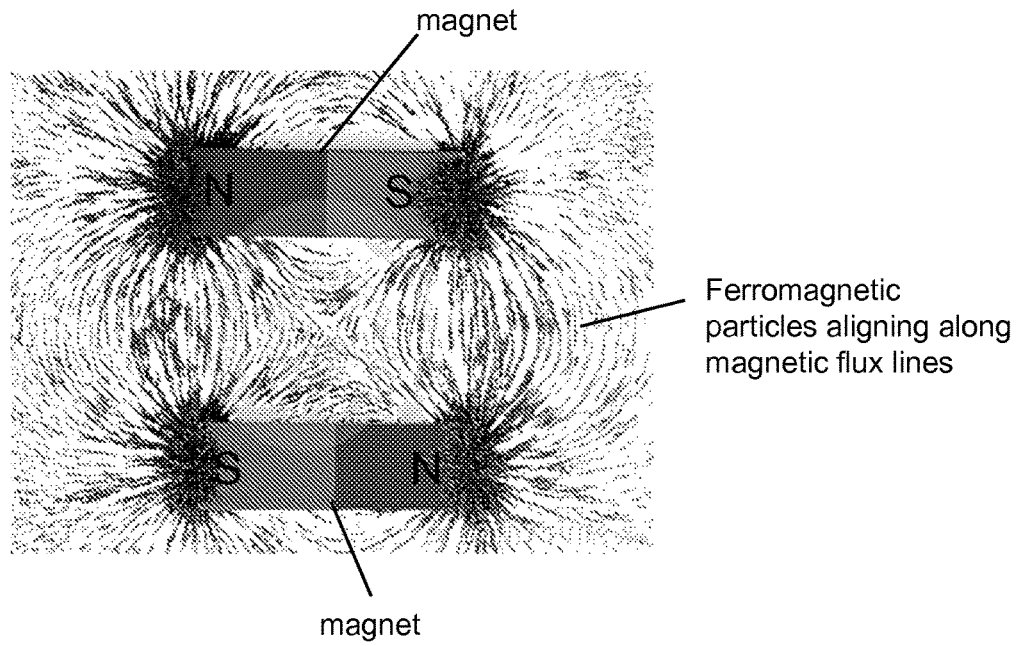
Figure 1G:
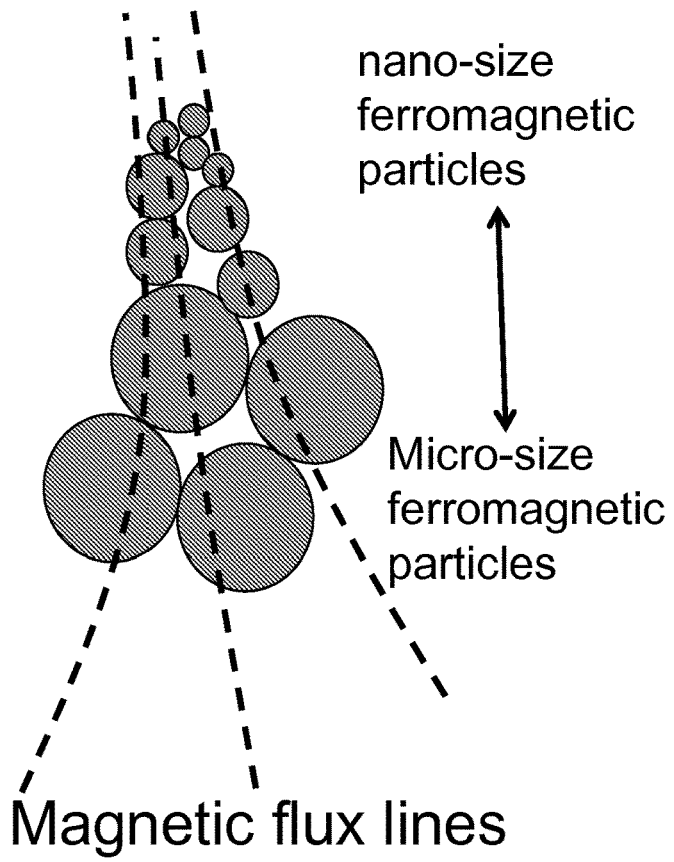

In some embodiments, the magnetic field gradient concentrating particles can form magnetic micro- or nano-structures on at least a portion of the fluid-contact surface of the magnetic separation chamber in the presence of a magnetic field gradient. The magnetic micro- or nano-structures can be two dimensional or three dimensional. The magnetic micro- or nano-structures are formed on the fluid-contact surface or magnetic capture surface that is exposed to a magnetic field gradient. By way of example only, FIG. 1D or FIG. 1E shows magnetic field gradient concentrating particles forming protruding or spiky magnetic micro- or nano-structures on a fluid-contact surface or magnetic capture surface.

The magnetic field gradient concentrating particles are substantially aligned along the magnetic flux lines of a magnetic field. As used herein, the term "substantially aligned" includes perfect alignment as well as alignment with slight deviation from magnetic flux lines of a magnetic field. Perfect alignment refers to perfect alignment of the magnetic field gradient concentrating particles along the magnetic flux lines of a magnetic field. In some embodiments, the alignment between the magnetic field gradient concentrating particles and magnetic flux lines of a magnetic field can have a deviation of less than 45° (including, e.g., less than 40°, less than less than 35°, less than 30°, less than 25°, less than 20°, less than 15°, less than 10°, or less than) 5° as compared to perfect alignment. For example, FIG. 1D shows that the magnetic field gradient concentrating particles are arranged such that they follow along the magnetic flux lines of a magnetic field generated by magnet(s). Exact magnetic flux lines can be determined by computational stimulation. The farther away the magnetic flux lines from a magnetic source, the weaker the magnetic strength to fix a magnetic flux density gradient concentrating particle in space. Thus, the size of the magnetic micro- or nano-structure can vary with the magnetic strength of a magnetic source. By aligning along with magnetic flux lines of the magnetic field, the magnetic energy of the magnetic field gradient concentrating particles is minimized. In some embodiments, the magnetic field gradient concentrating particles can form a fractal structure on at least a portion of the fluid-contact surface, which enables generation of stronger magnetic forces around the magnetic field gradient concentrating particles. As used herein, the term "fractal structure" refers to a structure having a repeating pattern that displays at every scale or at every level. A fractal structure is a type of ordered structures, as distinguished from random structures, which are not ordered.

The magnetic field gradient concentrating particles dispersed or distributed on the fluid-contact surface or magnetic capture surface act as magnetic field gradient concentrators. The "magnetic field gradient concentrators" increase magnetic flux density gradients locally experienced by magnetic particles (e.g., target-binding magnetic particles) in a fluid or a fluid sample by at least about 10% or more, as compared to the magnetic flux density gradients experienced by the magnetic particles (e.g., target-binding magnetic particles) in the absence of the magnetic field gradient concentrators. As used herein, the term "local" or "locally" refers to the magnetic flux density gradients in the area or space surrounding or nearby the magnetic field gradient concentrating particles as experienced by the magnetic particles or target-binding magnetic particles in a fluid, when they flow past or are in proximity to the magnetic field gradient concentrators. The size of the local effect can be determined as a function of a number of factors, including, e.g., but not limited to the applied magnetic field strength, and/or the size and/or arrangement of the magnetic field gradient concentrating particles. In some embodiments, the increase in the local magnetic flux density gradients experienced by the magnetic particles (e.g., target-binding magnetic particles) can be at least about 20% or more, including, e.g., at least about 30%, at least about 40%, at least about 50%, at least about 60%, at least about 70%, at least about 80%, at least about 90%, at least about 95% or more, higher than that in the absence of the magnetic field gradient concentrators. In some embodiments, the increase in the local magnetic flux density gradients experienced by the magnetic particles (e.g., target-binding magnetic particles) can be at least about 1.1-fold or more, including, e.g., at least about 1.2-fold, at least about 1.3-fold, at least about 1.4-fold, at least about 1.5-fold, at least about 2-fold, at least about 3-fold, at least about 4-fold, at least about 5-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 150-fold, at least about 200-fold, at least about 300-fold, at least about 400-fold, at least about 500-fold, at least about 1000-fold or more, higher than that in the absence of the magnetic field gradient concentrators. In some embodiments, the increase in the local magnetic flux density gradients experienced by the magnetic particles (e.g., target-binding magnetic particles) can be about 10-fold to about 200-fold, or about 10-fold to about 100-fold, higher than that in the absence of the magnetic field gradient concentrators.

By locally increasing the magnetic flux density or magnetic force around the magnetic particles (e.g., target-binding magnetic particles), the efficiency of separating magnetic particles from a fluid and thereby capturing or removing from a fluid at least one or more target molecules that are bound to target-binding magnetic particles is enhanced, even when the magnetic particles with weak magnetic moments (e.g., small magnetic nanoparticles) are used. In some embodiments, at least about 50% or more, including, e.g., at least about 60%, at least about 70%, at least about 80%, at least about 90%, at least about 95%, at least about 98%, or higher and up to 100% of the target-binding magnetic particles are attracted and bound to the magnetic field gradient concentrating particles distributed or dispersed on the fluid-contact surface or magnetic capture surface. In one embodiment, at least about 50% or higher of the target-binding magnetic particles (e.g., small magnetic nanoparticles) are attracted and bound to the magnetic field gradient concentrating particles distributed or dispersed on the fluid-contact surface or magnetic capture surface. In one embodiment, at least about 90% or higher of the target-binding magnetic particles (e.g., small magnetic nanoparticles) are attracted and bound to the magnetic field gradient concentrating particles distributed or dispersed on the fluid-contact surface or magnetic capture surface. In one embodiment, at least about 95% or higher of the target-binding magnetic particles (e.g., small magnetic nanoparticles) are attracted and bound to the magnetic field gradient concentrating particles distributed or dispersed on the fluid-contact surface or magnetic capture surface.

Therefore, the methods of various aspects described herein increases the efficiency of capturing, separating, or removing one or more target species (e.g., at least one, at least two or more target species) from a fluid or fluid sample by at least about 30% (including, e.g., at least about 60%, at least about 70%, at least about 80%, at least about 90%) or more, as compared to the efficiency in the absence of the magnetic field concentrating particles. In some embodiments, the efficiency of capturing, separating, or removing one or more target species (e.g., at least one, at least two or more target species) from a fluid or fluid sample can be increased by at least about 1.1-fold (including, e.g., at least about 1.5-fold, at least about 2-fold, at least about 3-fold, at least about 4-fold) or more, as compared to the efficiency in the absence of the magnetic field concentrating particles.

In the presence of a magnetic field gradient, the magnetic field gradient concentrating particles disperse and conform to at least a portion of a fluid-contact surface of the magnetic separation chamber or a magnetic capture surface. Therefore, the methods of various aspects described herein are amenable to a wide range of magnetic separation devices in various configurations. The magnetic separation device comprises a magnetic separation chamber or a magnetic capture surface as defined herein. As used herein, the term "magnetic separation chamber" refers to a chamber or space subjected to exposure of a magnetic field gradient and comprising at least one inlet for introduction of a fluid, and optionally at least one outlet for exit of the fluid. In some embodiments, the inlet can be used as an outlet for exit of a fluid. The magnetic separation chamber includes a fluid-contact surface that is subjected to exposure of a magnetic field gradient. For example, the magnetic separation chamber can comprise a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a hollow fiber, or any combinations thereof. Thus, the magnetic separation chamber can be of any shape and/or any size. In one embodiment, the fluid-contact surface of the magnetic separation chamber is a surface within a channel or a microchannel. In one embodiment, the fluid-contact surface of the magnetic separation chamber is a surface of a microwell. In one embodiment, the fluid-contact surface of the magnetic separation chamber is a surface of a magnetic solid substrate (e.g., in a form of a protruding structure such as a tip) that is brought into contact with a fluid.

Figure 6B:
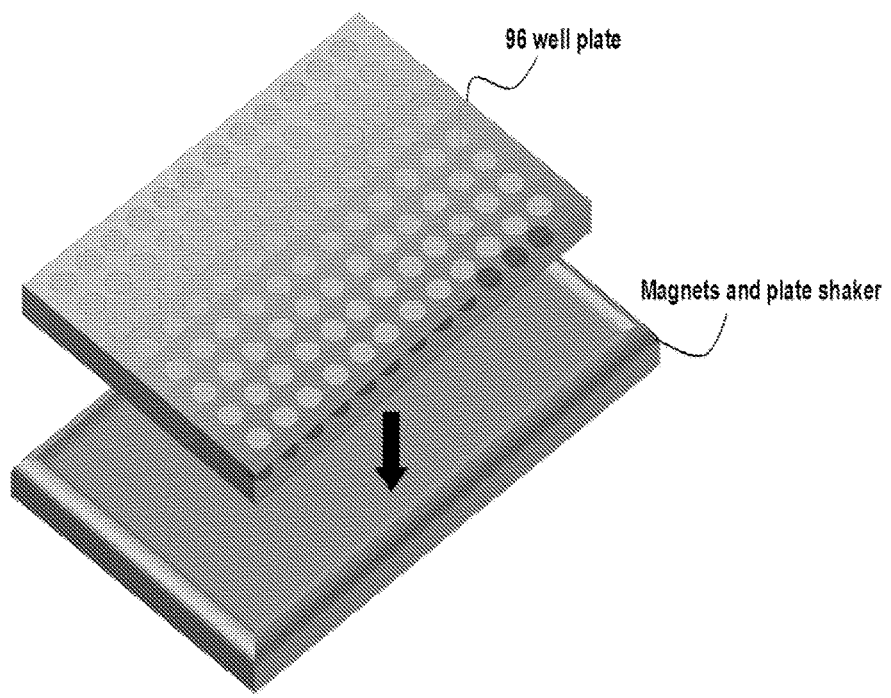
Figure 6C:
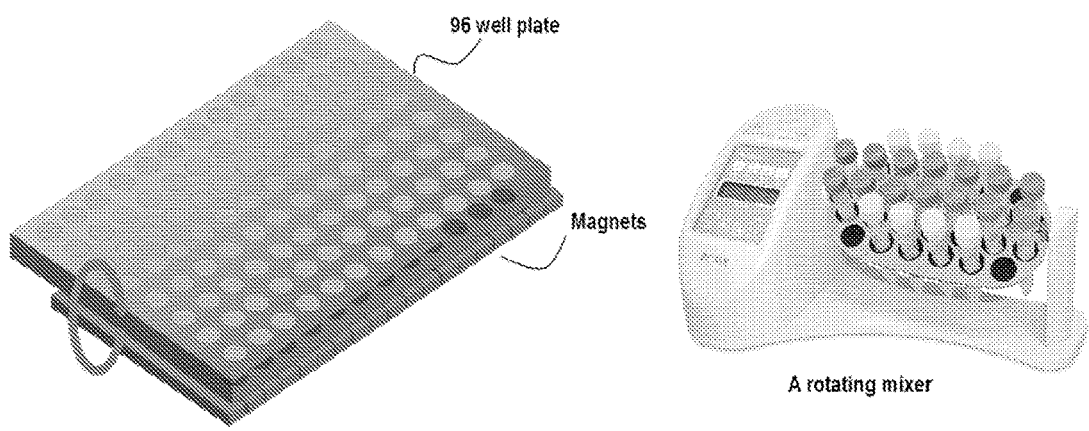

In some embodiments, the magnetic separation chamber is a non-fluidic chamber, in which a fluid remains in the chamber and does not flow through the chamber. Examples of a non-fluidic chamber include, without limitations, a multi-well plate, a flask (e.g., a tissue culture flask), a tube (e.g., eppendorf tubes, or tubes with an opening), any sample carriers, and combinations thereof. Thus, in some embodiments, the methods described herein can be applied to non-fluidic magnetic separation applications. By way of example only, the methods described herein can be used with a commercially available non-fluidic device, e.g., a magnetic column (e.g., Miltenyi®). The magnetic field gradient concentrating particles can be used in place of steel or iron wool and dispersed on the interior surface of the column in the presence of a magnetic field gradient, followed by adding a fluid sample comprising target-binding magnetic particles described herein. Another example of a non-fluidic chamber for use in the method described herein is a multi-well plate (e.g., 96-well plate), where the magnetic field gradient concentrating particles formed 2D or 3D magnetic nano- or micro-structures on the fluid-contact surface within the wells (e.g., on the magnetic tips of the movable multi-well tip comb brought into the wells as shown in FIG. 6A, or the well surface experiencing a magnetic field gradient as shown in FIGS. 6B-6C).

In some embodiments, the magnetic separation chamber is a fluidic chamber, which allows a fluid flowing therethrough. Examples of a fluidic chamber include, without limitations, a channel, a microfluidic channel, a hollow fiber, a hollow tube. Thus, in some embodiments, the method described herein can be applied to fluidic magnetic separation applications, e.g., as described in the Examples using a microfluidic device for magnetic separation. See, e.g., WO/2011/091037, WO/2012/135834, and WO 2013/126774, the contents of which are incorporated herein by reference, for additional microfluidic devices that can be used with the method described herein.

In some embodiments where the magnetic separation chamber is a fluidic chamber, the fluid can be introduced to the chamber at any flow rate, for example, depending on the volume capacity of the magnetic separation chamber, magnetic properties of the magnetic field gradient concentrating particles and/or target-binding magnetic particles, and/or the magnetic field gradient. In some embodiments, the fluid can be introduced to the chamber at a flow rate of about 0.1 mL/hr to about 100 L/hr. In some embodiments, the fluid can be introduced to the chamber at a flow rate of about 0.5 mL/hr to about 50 L/hr. In some embodiments, the fluid can be introduced to the chamber at a flow rate of about 1 mL/hr to about 10 L/hr. In some embodiments, the fluid can be introduced to the chamber at a flow rate of about 50 mL/hr to about 10 L/hr. In some embodiments, the fluid can be introduced to the chamber at a flow rate of about 1 L/hr to about 100 L/hr. In some embodiments, the fluid can be introduced to the chamber at a flow rate of about 1 L/hr to about 50 L/hr. In some embodiments, the fluid can be introduced to the chamber at a flow rate of about 50 mL/hr to about 10 L/hr.

In accordance with the methods of various aspects described herein, the magnetic field gradient concentrating particles are dispersed or distributed onto the fluid-contact surface or magnetic capture surface, prior to contacting the fluid-contact surface or magnetic capture surface with a fluid or a fluid sample comprising the target-binding magnetic particles. Thus, the fluid to be brought into contact with the fluid-contact surface or magnetic capture surface can comprise the target-binding magnetic particles but does not contain magnetic field gradient concentrating particles suspended in the same fluid. One of the advantages of the method described herein is that the fluid can be introduced into the chamber at high flow rates, enabling a high-throughput separation process. On the other hand, if the magnetic field gradient concentrating particles and target-binding magnetic particles were to be suspended in the same fluid during magnetic capture, the magnetic separation efficiency would be low at high flow rates. It is because in the presence of a magnetic field gradient, the magnetic field gradient concentrating particles and target-binding magnetic particles could migrate differently in the fluid, for example, due to a difference in magnetic drag velocity. By way of example only, when a fluid containing larger magnetic field gradient concentrating particles (e.g., ~1 µm in diameter) and smaller target-binding magnetic particles (e.g., ~128 nm) were to be flowed at high flow rates (e.g., ~100 mL/s to ~1000 mL/s) in the presence of a magnetic field gradient, the larger magnetic field gradient concentrating particles would have much faster magnetic drag velocity and thus be attracted to a surface and pulled away from the target-binding magnetic particles. Therefore, the magnetic field gradient concentrating particles were not able to act as magnetic field gradient concentrators for the target-binding magnetic particles.

In one embodiment, prior to contacting the fluid-contact surface or magnetic capture surface with the fluid comprising target-binding magnetic particles, the method can further comprise distributing or dispersing the magnetic field gradient concentrating particles onto at least a fluid-contact surface or magnetic capture surface. The magnetic field gradient concentrating particles conform to the fluid-contact surface or magnetic capture surface. To do this, for example, the magnetic field gradient concentrating particles suspended in a buffer or an organic solvent (e.g., ethanol) can be introduced into a magnetic separation chamber while a magnetic field gradient is present to attract or trap the magnetic field gradient concentrating particles onto at least a portion of the fluid-contact surface of the magnetic separation chamber. Methods to produce a magnetic field gradient to attract magnetic particles are known in the art. Once the magnetic field gradient concentrating particles are trapped in the magnetic separation chamber or trapped on a magnetic capture surface, the magnetic field gradient can be manipulated to distribute or disperse those magnetic field gradient concentrating particles over the fluid-contact surface area in a desired manner (e.g., uniform distribution, random distribution, or in a specific pattern). The magnetic field gradient concentrating particles are magnetized and substantially aligned along the magnetic flux lines of a magnetic field. In one embodiment, at least one or more permanent magnets can be placed around the magnetic separation chamber or be placed on at least one side of a magnetic capture surface and be manipulated to distribute or disperse those magnetic field gradient concentrating particles over the fluid-contact surface area in a desired manner (e.g., uniform distribution, random distribution, or in a specific pattern).

In some embodiments, the method can comprise collecting target-bound target-binding magnetic particles, for example, for subsequent analysis or analyses, including, e.g., but not limited to, ELISA, optical imaging, spectroscopy, polymerase chain reaction (PCR), mass spectrometric methods, immunoassays, and any combinations thereof. Prior to the analysis, the target-bound target-binding magnetic particles can be released from the magnetic field gradient concentrating particles, for example, by fluid shear stress, or demagnetizing the magnetic field gradient concentrating particles and/or target-bound target-binding magnetic particles.

In some embodiments, the method can comprise subjecting the fluid, upon magnetic capture of the target-bound target-binding magnetic particles, to at least a detection assay or analysis to determine if a target molecule has been captured or removed by the target-binding magnetic particles.

By having one or a plurality of (e.g., at least 2, at least 3 or more) different target-binding magnetic particles in a fluid, the method described herein can be adapted to capture or remove or capture at least one type of target molecules or a plurality of (e.g., at least 2, at least or more) different types of target molecules from the fluid. In some embodiments, different target-binding magnetic particles can be added to the fluid all at once and the fluid is then subjected to magnetic separation using the method as described herein to remove or capture various target molecules. By varying at least one or more parameters of magnetic separation, including, e.g., flow rate of the fluid, the strength and/or duration of the magnetic field gradient, and/or the magnetic properties and/or size of the target-binding magnetic particles and/or magnetic field gradient concentrating particles, different types of target-bound target-binding magnetic particles can be selectively attracted to the magnetic field gradient concentrating particles that are distributed on the fluid-contact surface. By way of example only, where target-binding magnetic particles of different sizes are used to bind distinct target molecules, different sized target-binding magnetic particles can be pulled to a fluid-contact surface (comprising the magnetic field gradient concentrating particles distributed thereon) at different rates. In a fluidic magnetic separation device, different sized target-binding magnetic particles (with the corresponding target molecules bound thereto) can be fluid dynamically aligned in a certain portion of a fluidic channel prior to magnetic separation. Fluid dynamically alignment is based on a principle called inertia hydrodynamic focusing that has been used for sheathless focusing of particles in channels. As a fluid flows through the magnetic separation chamber in the presence of a magnetic field gradient, the target-binding magnetic particles of different sizes in the fluid can be pulled to different portions of a fluid-contact surface of the magnetic separation chamber. Accordingly, in these embodiments, different types of target molecules can be selectively captured or removed from the fluid using target-binding magnetic particles of different sizes. As such, in some embodiments, the methods described herein can comprise, prior to magnetic separation, pre-aligning the target-binding magnetic particles of different sizes within a fluidic channel such that they will flow from the same starting line within the fluidic channel when they are exposed to a magnetic field gradient. Depending on the size of the magnetic particles and/or the magnetic force acting on them, the target-binding magnetic particles of different sizes can be selectively pulled to different portions of the fluid-contact surface comprising magnetic field gradient concentrating particles distributed thereon. The bound target-binding magnetic particles can be collected afterward.

In alternative embodiments, different target molecules can be individually captured or removed from the fluid in a sequential manner. For example, a first type of target molecules can be first captured or removed by adding a first type of target-binding magnetic particles to the fluid for magnetic separation using the method as described herein. Capture or removal of a second type of target molecules from the fluid can follow by repeating the method described herein with a second type of target-binding magnetic particles.

The methods of various aspects described herein can be utilized to capture or remove any target molecules of interest in any fluid. Non-limiting examples of the target molecules that can be captured or removed using the method described herein include cells, proteins, nucleic acids, microbes, small molecules, chemicals, toxins, drugs, and any combinations thereof. In one embodiment, the method described herein is adapted to capture or remove a microbe from a fluid.

The magnetic field source used in the methods of various aspects described herein can be any magnet device that can be positioned to generate a magnetic field gradient for trapping magnetic field gradient concentrating particles on a fluid-contact surface or a magnetic capture surface and thereby increasing local magnetic field gradient experienced by a magnetic particle (e.g., a target-binding magnetic particle). An electromagnetic controller can be used to control and adjust the magnetic field and gradients thereof, and to control the distribution of the magnetic field gradient concentrating particles on a fluid-contact surface or a magnetic capture surface. The magnetic field gradient can be generated by a permanent magnet or by an electromagnetic signal generator. The electromagnetic signal generator can include an electromagnet or electrically-polarizable element, or at least one permanent magnet. The magnetic field gradient can be produced at least in part according to a pre-programmed pattern. The magnetic field gradient can have a defined magnetic field strength and/or spatial orientation. In some embodiments, the magnetic field gradient has a defined magnetic field strength.

As used herein, the term "magnetic field" refers to magnetic influences which create a local magnetic flux that flows through a composition and can refer to field amplitude, squared-amplitude, or time-averaged squared-amplitude. It is to be understood that magnetic field can be a direct-current (DC) magnetic field or alternating-current (AC) magnetic field. The magnetic field strength can range from about 0.00001 Tesla per meter (T/m) to about $10^5$ T/m. In some embodiments, the magnetic field strength can range from about 0.0001 T/m to about $10^4$ T/m. In some other embodiments, the magnetic field strength can range from about 0.001 T/m to about $10^3$ T/m.

Microbe capture from a fluid: In some embodiments, the methods of various aspects described herein can be used to capture or remove at least one or more microbes from a fluid. In some embodiments, the methods described herein can be used in combination with any methods for capturing or removing microbe(s) from a fluid using microbe-binding magnetic particles described in WO/2011/090954 and WO/2013/012924, contents of both of which are incorporated herein by reference in their entireties. For example, the fluid-contact surface of the microbe capture devices (e.g., comprising a non-fluidic or fluidic magnetic separation chamber as described herein) can be distributed or dispersed with magnetic field gradient concentrating particles to form magnetic nano- or micro-structures, prior to introduction of a fluid having or suspected of having microbe(s).

In some embodiments, the methods described herein can be performed in a microbe diagnostic device or blood cleansing device as described in Int. Pat. App. No. WO 2011/091037, filed Jan. 19, 2011, and/or WO 2012/135834 filed Apr. 2, 2012, the contents of which are incorporated herein by reference in their entireties. In these embodiments, the fluid-contact surface of the microbe diagnostic device or blood cleansing device can be distributed or dispersed with magnetic field gradient concentrating particles to form magnetic nano- or micro-structures, prior to introduction of a fluid having or suspected of having microbe(s). A microbe diagnostic device as described in Int. Pat. App. No. WO 2011/091037, filed Jan. 19, 2011, can also be modified to replace the capture chamber or capture and visualization chamber with an s-shaped flow path. A magnet can then be used to capture bound microbe against the flow path wall; separating the bound microbe from rest of the fluid.

In some embodiments, the methods described herein can be performed in a device and/or in combination with a method as described in U.S. Pat. App. Pub. No. 2009/0220932, No. 2009/007861, No. 2010/0044232, No. 2007/0184463, No. 2004/0018611, No. 2008/0056949, No. 2008/0014576, No. 2007/0031819, No. 2008/0108120, and No. 2010/0323342, the contents of which are all incorporated herein by reference.

Magnetic Field Gradient Concentrating Particles

As described earlier, the magnetic field gradient concentrating particles are magnetic particles that act as local magnetic field gradient concentrators to increase the local magnetic flux density gradient experienced by a magnetic particle (e.g., a target-binding magnetic particle) in a magnetic separation chamber and hence increase efficiency of separating or capturing target-binding magnetic particles from a fluid. The term "magnetic field gradient" as used herein refers to a variation in the magnetic field with respect to position. By way of example only, a one-dimensional magnetic field gradient is a variation in the magnetic field with respect to one direction, while a two-dimensional magnetic field gradient is a variation in the magnetic field with respect to two directions. The magnetic field gradient can be static or transient (dynamic). For example, a transient magnetic field gradient can be a rotating or translational magnetic field gradient.

Magnetic field gradient concentrating particles can be commercially available magnetic particles of desired sizes. Magnetic particles (including nanoparticles or microparticles) are well-known and methods for their preparation have been described in the art. See, e.g., U.S. Pat. Nos. 6,878,445; 5,543,158; 5,578,325; 6,676,729; 6,045,925; and 7,462,446; and U.S. Patent Publications No. 2005/0025971; No. 2005/0200438; No. 2005/0201941; No. 2005/0271745; No. 2006/0228551; No. 2006/0233712; No. 2007/01666232; and No. 2007/0264199.

The magnetic field gradient concentrating particles can comprise superparamagnetic particles, paramagnetic particles, ferrimagnetic particles, ferromagnetic particles, or combinations thereof. The term "paramagnetic" as used herein means a material with a small but positive magnetic susceptibility (magnetigability). Paramagnetic particles are attracted by an external magnetic field, and form internal, induced magnetic fields in the direction of the applied magnetic field. However, paramagnetic materials do not retain any magnetization in the absence of an external magnetic field. Examples of paramagnetic materials that can be included in the magnetic field gradient concentrating particles include, without limitations, metal ions (e.g., $Gd^{3+}$, $Fe^{3+}$, $Mn^{2+}$, and $Cu^{2+}$), transition metals, such as titanium, vanadium, chromium, manganese, iron cobalt, nickel, copper, and compounds thereof; lanthanide metals, such as europium and gadolinium, and compounds thereof; rare earth elements and compounds thereof; free radicals, such as nitroxides and compounds thereof; and actinide metals, such as protactinium, and compounds thereof.

As used herein, the term "ferromagnetic" refers to a substance, such as iron particles, having a large positive magnetic susceptibility. These particles possess a large magnetic moment and are able to relax neighboring nuclei much faster than paramagnetic ions. They possess large magnetic moments even in weak external fields and produce large local magnetic flux densities. Unlike paramagnetic materials, ferromagnetic materials retain magnetization even when the external magnetic field gradient is removed. Ferromagnetic materials that can be included in the magnetic field gradient concentrating particles include, but are not limited to, iron oxides, such as $Fe_2O_3$, reduced iron, iron powder, atomized iron, electrolyte iron, cobalt, nickel, permalloy, alloys comprising at least one or more ferromagnetic materials described herein, some compounds of rare earth metals, some minerals such as iodestone, and a combination of two or more thereof. There are a number of methods to manufacture iron particles. Reduced iron is also called sponge iron because it contains sponge-like hollow spaces inside the particles. Atomization of iron (atomized iron) can be made by forcing a molten metal stream (e.g., a molten stream comprising iron) through a narrow duct at high pressure.

In some embodiments, magnetite particles are ferromagnetic when their sizes are above a certain threshold, e.g., 10 nm. When the magnetite particle sizes are below 10 nm, the magnetized vector becomes unstable, and the magnetic property is no longer ferromagnetic but "superparamagnetic."

In one embodiment, the magnetic field gradient concentrating particles are ferromagnetic particles. In one embodiment, the ferromagnetic particles comprise atomized iron. Ferromagnetic materials or particles generally exhibit a larger magnetic permeability than paramagnetic materials, and are thus able to keep magnetic fields within themselves when they are exposed to an external magnetic field. In the absence of an external magnetic field, the magnetic domains of ferromagnetic materials stay randomly oriented due to thermal fluctuations. However, they become substantially aligned parallel under the applied magnetic fields. The magnetic fields converge into ferromagnetic materials or particles due to their high magnetic permeability to reduce the magnetic energy, and the ferromagnetic materials or particles then generate high magnetic flux density gradient by having magnetic fields diverge into the surrounding free space, thus providing stronger magnetic forces.

By the term "superparamagnetic" is meant a material that is highly magnetically susceptible, i.e., it becomes strongly magnetic when placed in a magnetic field, like in ferromagnetism; however, like a paramagnetic material, a superparamagnetic material rapidly loses its magnetism and displays no remanence once the magnetic field is removed.

As used herein, the term "ferrimagnetic" includes materials that have populations of atoms with opposing magnetic moments, as in antiferromagnetism; however, in ferrimagnetic materials, the opposing moments are unequal and a spontaneous magnetization remains. Examples of ferrimagnetic materials that can be included in the magnetic field gradient concentrating particles include, but are not limited to ferrites, magnetic garnets, magnetite (iron (II, III) oxide), yttrium iron garnet, cubic ferrites comprising iron oxides and other elements such as aluminum, cobalt, nickel, manganese and zinc, hexagonal ferrites such as $PbFe_{12}O_{19}$ and $BaFe_{12}O_{19}$, and pyrrhotite, $Fe_{1-x}S$.

The magnetic field gradient concentrating particles can be selected for any size, e.g., depending on the dimensions of the magnetic separation chamber and/or area of the fluid-contact surface. For example, the size of the magnetic field gradient concentrating particles can be smaller than (e.g., by at least 10% or more), comparable to (e.g., within 10%, or within 5%), or larger than (e.g., by at least 10% or more) that of the target-binding magnetic particles described herein. In some embodiments, the magnetic field gradient concentrating particles are larger than the target-binding magnetic particles. In some embodiments, the size (e.g., diameter) of the magnetic field gradient concentrating particles are larger than the size (e.g., diameter) of the target-binding magnetic particles by at least about 30%, at least about 40%, at least about 50%, at least about 60%, at least about 70%, at least about 80%, at least about 90%, at least about 95%, at least about 98%, or more. In some embodiments, the size (e.g., diameter) of the magnetic field gradient concentrating particles are larger than the size of the target-binding magnetic particles by at least about 1-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 50-fold, at least about 100-fold, at least about 1000-fold or higher.

In some embodiments, the magnetic field gradient concentrating particles are smaller than the target-binding magnetic particles. In some embodiments, the size (e.g., diameter) of the magnetic field gradient concentrating particles are smaller than the size (e.g., diameter) of the target-binding magnetic particles by at least about 30%, at least about 40%, at least about 50%, at least about 60%, at least about 70%, at least about 80%, at least about 90%, or more. When the magnetic field gradient concentrating particles are smaller than the target-binding magnetic particles in size, the magnetic field gradient concentrating particles can aggregate and form magnetic micro- or nano-structures once they are exposed to an applied magnetic field.

In some embodiments, the size (e.g., diameter) of the magnetic field gradient concentrating particles ranges from about 50 nm to about 5 mm, from about 100 nm to about 3 mm, from about 1 μm to about 1 mm. In one embodiment, the diameter of the magnetic field gradient concentrating particles is about 300 μm.

The magnetic field gradient concentrating particles can be of any shape, including but not limited to spherical, rod, elliptical, cylindrical, and disc. In some embodiments, magnetic field gradient concentrating particles having a substantially spherical shape and defined surface chemistry can be used to minimize chemical agglutination and non-specific binding.

In some embodiments, the magnetic field gradient concentrating particles can be functionalized or unfunctionalized. In some embodiments, the magnetic field gradient concentrating particles can be functionalized (e.g., by conjugating a chemical functional group or a molecule to the magnetic field gradient concentrating particles). By way of example only, in some embodiments, the magnetic field gradient concentrating particles can be functionalized with molecules that allow target-binding magnetic particles to remain bound to the magnetic field gradient concentrating particles in the absence of a magnetic field. Target-binding magnetic particles are attracted to the magnetic field gradient concentrating particles when a magnetic field is applied. After the magnetic field is removed, the magnetic attraction between the magnetic field gradient concentrating particles and the target-binding magnetic particles can decrease over time, or become insufficient to withstand external shear stress introduced during an assay. Functionalization of the magnetic field gradient concentrating particles can inhibit or minimize the likelihood of target-binding magnetic particles that were attracted to the magnetic field gradient concentrating particles to release from the surface of the magnetic field gradient concentrating particles, when a magnetic field is removed, and/or during the course of an assay, e.g., various wash procedures of ELISA or immunoassays. This can help increasing the accuracy and/or sensitivity of an assay for detection of target molecules in a fluid.

In some embodiments, the magnetic field gradient concentrating particles can be unfunctionalized, e.g., magnetic particles with no active functional groups on their surfaces for conjugation or any other reaction with the surrounding.

In some embodiments, the magnetic field gradient concentrating particles can be modified to inhibit non-specific binding of target molecules to the magnetic field gradient concentrating particles.

In some embodiments of this aspect and other aspects described herein, the magnetic field gradient concentrating particles by themselves are not able to bind or capture a target. In some embodiments of this aspect and other aspects described herein, the magnetic field gradient concentrating particles do not comprise metal oxide (e.g., iron oxide). In some embodiments, the magnetic field gradient concentrating particles can be treated to reduce non-specific interaction, for example, by at least about 30% or more (including, e.g., at least about 40%, at least about 50%, at least about 60%, at least about 70%, at least about 80%, at least about 90%, at least about 95% or more), with a target to be removed or separated from a fluid. This can improve selectivity of the methods, kits, or solid substrates described herein to capture, remove, or separate target molecule(s) from a fluid. For example, in some embodiments, the magnetic field gradient concentrating particles can be treated with a blocking agent, e.g., to reduce their non-specific interaction with a target to be removed or separated from a fluid. Non-limiting examples of a blocking agent include a lubricant (e.g., but not limited to silicone, or mold-release agent), a polymer (e.g., but not limited to silicon-based polymer such as polydimethylsiloxane (PDMS)), milk proteins, bovine serum albumin, blood serum, whole blood, and a combination of two or more thereof.

In some embodiments of this aspect and other aspects described herein, the magnetic field gradient concentrating particles by themselves can bind or capture a target molecule or species to be captured, removed, or separated from a fluid. In some embodiments, the magnetic field gradient concentrating particles can be adapted or modified to bind or capture a target molecule or species to be captured, removed, or separated from a fluid. In some embodiments where the magnetic field gradient concentrating particles have target-binding capability, using both target-binding magnetic particles and magnetic field gradient concentrating particles in the methods, devices, kits, and/or solid substrates described herein can produce a synergistic effect in capturing, removing, or separating a target molecule or species from a fluid. In some embodiments where the magnetic field gradient concentrating particles have target-binding capability, using both target-binding magnetic particles and magnetic field gradient concentrating particles in the methods, devices, kits, and/or solid substrates described herein can produce an additive effect in capturing, removing, or separating a target molecule or species from a fluid.

Magnetic Particles and Target-binding Magnetic Particles

As used herein, the term "magnetic particle" refers to a particle that can be magnetically attracted to one or more magnetic field gradient concentrating particles when the magnetic field gradient concentrating particle(s) is/are subjected to a magnetic field gradient.

As used herein, the term "target-binding magnetic particle" refers to a magnetic particle adapted to specifically bind at least one or more target molecules described herein. For example, the exterior surface of the magnetic particle comprises target-binding molecules conjugated thereto. Depending upon applications of the method described herein, the target-binding magnetic particles can be adapted to bind one or more target molecules in any type of fluid described herein.

As used herein, the term "specifically binds" refers to the ability of a target-binding magnetic particle or target-binding molecule to bind to a specific target species or molecule with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if a microbe-binding molecule (e.g., MBL or a functional fragment thereof) binds to a microbe and/or microbe-associated molecular pattern (MAMP) with a $K_D$ of $10^{-5}$ M or lower, but not substantially to molecules that are not microbes or MAMPs, then the agent is said to specifically bind the microbe and/or MAMP. By "not substantially" is meant that the $K_D$ for target molecules, as determined, e.g., by competition assay or by other means known in the art, is at least $10^2$-fold lower than that for other non-target molecules, and preferably at least $10^3$-fold lower, at least $10^4$-fold lower, $10^5$-fold lower or less. Specific binding can be influenced by, for example, the affinity and avidity of the target-binding molecules and the concentration of the target-binding molecules and/or target-binding magnetic particles used. A person of ordinary skill in the art can determine appropriate conditions under which the target-binding magnetic particles described herein selectively bind using any suitable methods, such as titration of target-binding magnetic particles in a suitable assay and depletion efficiency of the target from a sample, such as those described herein in the Examples.

In some embodiments, at least a portion of the target-binding magnetic particles can have the corresponding target molecules bound thereto. In some embodiments, at least a portion of the target-binding magnetic particles do not have any target molecules bound thereto.

The target-binding magnetic particles can be paramagnetic, superparamagnetic, or ferromagnetic. In some embodiments, the target-binding magnetic particles can be paramagnetic or superparamagnetic. In some embodiments, the target-binding magnetic particles can have the same core magnetic particles as the magnetic field gradient concentrating particles, optionally with different surface properties, e.g., surface chemistry and/or composition. In other embodiments, the core magnetic particles within the target-binding magnetic particles can be different from that of the magnetic field gradient concentrating particles.

In some embodiments, the target-binding magnetic particles can be target-binding magnetic particles with weak magnetic moments that they cannot be efficiently captured or removed from the fluid in the presence of an external magnetic field without the magnetic field gradient concentrating particles described herein or using the existing magnetic separation techniques. Magnetic moment or magnetic dipole moment (M) is proportional to magnetic susceptibility ($\chi$) (M=$\chi$*H, where H is applied magnetic field strength). Accordingly, in some embodiments, the target-binding magnetic particles can be target-binding magnetic particles with magnetic susceptibility ranging from less than 1 emu/g to about 100 emu/g. In some embodiments, the target-binding magnetic particles can be target-binding magnetic particles with magnetic susceptibility of about less than 1 emu/g to about 80 emu/g, or about 5 emu/g to about 75 emu/g. In some embodiments, the target-binding magnetic particles can be target-binding magnetic particles with magnetic susceptibility of about 40 emu/g to about 50 emu/g. For example, iron oxide nano- or micro-particles smaller than 4 μm can have an increased magnetic separation efficiency when they work with the magnetic field gradient concentration particles described herein.

While any size (e.g., ranging from about 1 nm to about 1 mm) of the target-binding magnetic particles can be used in the method described herein, the methods of various aspects described herein can provide an effective solution to magnetic separation with small target-binding magnetic particles (or magnetic particles with weak magnetic moments), because the existing magnetic separation methods generally do not work or yield a low magnetic separation efficiency with small target-binding magnetic particles due to their weak magnetic moments. Accordingly, in some embodiments, the target-binding magnetic particles are nanoparticles. As used herein, the term "nanoparticle" refers to particles that are on the order of $10^{-9}$ or one billionth of a meter and below. Generally, nanoparticles have a diameter in the range from about 1 nm to about 1000 nm. The term "nanoparticle" includes e.g., but is not limited to, nanospheres; nanorods; nanoshells; and nanoprisms. In some embodiments, the diameter of the target-binding magnetic nanoparticles is no more than 250 nm, no more than 100 nm, no more than 50 nm, or no more than 5 nm.

In some embodiments, the target-binding magnetic particles are microparticles smaller than 10 μm, including, e.g., smaller than 5 μm, smaller than 4 μm, smaller than 3 μm, smaller than 2 μm, smaller than 1 μm or less.

In some embodiments, target-binding magnetic particles can comprise on their surfaces target-binding molecules. By "target-binding molecules" is meant herein molecules that can interact with or bind to a target species or a target molecule of interest such that the target species or target molecule can be captured or removed from a fluid. Typically the nature of the interaction or binding is noncovalent, e.g., by hydrogen, electrostatic, or van der Waals interactions, however, binding can also be covalent. Target-binding molecules can be naturally-occurring, recombinant or synthetic. Examples of the target-binding molecule can include, but are not limited to, a nucleic acid, an antibody or a portion thereof, an antibody-like molecule, an enzyme, an antigen, a small molecule, a protein, a peptide, a peptidomimetic, a carbohydrate, an aptamer, and any combinations thereof. By way of example only, for removal of microbes from a fluid, the target-binding molecule can be selected from the group consisting of: opsonins, lectins, antibodies, and antigen binding fragments thereof, proteins, peptides, peptidomimetics, carbohydrate-binding proteins, nucleic acids, carbohydrate, lipids, steroids, hormones, lipid binding molecules, cofactors, nucleosides, nucleotides, peptidoglycan, lipopolysaccharide-binding proteins, small molecules, and any combinations thereof. An ordinary artisan can readily identify appropriate target-binding molecules for each target species or target molecules of interest to be captured or removed from a fluid.

In some embodiments, the target-binding molecules can be modified by any means known to one of ordinary skill in the art. Methods to modify each type of target-binding molecules are well recognized in the art. Depending on the types of target-binding molecules, an exemplary modification includes, but is not limited to genetic modification, biotinylation, labeling (for detection purposes), chemical modification (e.g., to produce derivatives or fragments of the target-binding molecule), and any combinations thereof. In some embodiments, the target-binding molecule can be genetically modified. In some embodiments, the target-binding molecule can be biotinylated.

In some embodiments, the target-binding molecules can comprise on their surfaces microbe-binding molecules as described herein, and/or disclosed in WO/2011/090954 and WO/2013/012924, the contents of which are incorporated herein by reference. Accordingly, in some embodiments, the method described herein can be used with the target-binding magnetic particles for microbial capture, i.e., microbe-binding magnetic particles, e.g., but not limited to FcMBL magnetic particles. Examples of microbe-binding magnetic particles can include, but are not limited to the ones described in WO/2011/090954 and WO/2013/012924, the contents of which are incorporated herein by reference.

In some embodiments, the target-binding molecule can be an antibody or a portion thereof, or an antibody-like molecule. In some embodiments, the target-binding molecule can be an antibody or a portion thereof, or an antibody-like molecule that is specific for detection of a rare-cell, e.g., a circulating tumor cell, a fetal cell, a stem cell and/or a microbe biomarker. In some embodiments, the target-binding molecule can be an antibody or a portion thereof, or an antibody-like molecule that is specific for a protein or an antigen present on the surface of a rare cell, e.g., a circulating tumor cell, a fetal cell, a stem cell and/or a microbe. In such embodiments, the target-binding molecules can be used to, for example, detect and/or identify cell type or species (including normal and/or diseased cells), the presence of cell or disease markers, cellular protein expression levels, phosphorylation or other post-translation modification state, or any combinations thereof.

In some embodiments, the target-binding molecule can be a nucleic acid (e.g., DNA, RNA, LNA, PNA, or any combinations thereof). For example, the nucleic acid can encode the gene specific for a rare cell biomarker, e.g., a circulating tumor cell, a fetal cell, a stem cell and/or a microbe biomarker. In such embodiments, the nucleic acids can be used to determine, for example, the existence of characteristic cellular DNA or RNA sequences (such as in fluorescent in situ hybridization), RNA expression levels, miRNA presence and expression, and any combinations thereof, in various applications, e.g., for disease diagnose, prognosis and/or monitoring.

In some embodiments, the target-binding molecule can be a protein or a peptide. In some embodiments, the protein or peptide can be essentially any proteins that can bind to a rare cell, e.g., a circulating tumor cell, a fetal cell, a stem cell and/or a microbe. By way of example only, if the target species is a bacteria, exemplary proteins or peptides that can be used to generate microbe-binding molecules and/or microbe-binding magnetic particles can include, but are not limited to, innate-immune proteins (e.g., without limitations, MBL, Dectin-1, TLR2, and TLR4 and any molecules (including recombinant or engineered protein molecules) disclosed here as well as the microbe-binding molecules disclosed in the International Application Publication Nos. WO/2011/090954 and WO/2013/012924, the content of which is incorporated herein by reference) and proteins comprising the chitin-binding domain, and any factions thereof. Such innate-immune proteins and chitin-binding domain proteins can be used to detect their corresponding pattern-recognition targets (e.g., microbes such as bacteria) and fungus, respectively.

In some embodiments, the target-binding molecule can be an aptamer. In some embodiments, the target-binding molecule can be a DNA or RNA aptamer. The aptamers can be used in various bioassays, e.g., in the same way as antibodies or nucleic acids described herein. For example, the DNA or RNA aptamer can encode a nucleic acid sequence corresponding to a rare cell biomarker or a fraction thereof, for use as a target-binding molecule on the magnetic particles described herein.

In some embodiments, the target-binding molecule can be a cell surface receptor ligand. As used herein, a "cell surface receptor ligand" refers to a molecule that can bind to the outer surface of a cell. Exemplary cell surface receptor ligand includes, for example, a cell surface receptor binding peptide, a cell surface receptor binding glycopeptide, a cell surface receptor binding protein, a cell surface receptor binding glycoprotein, a cell surface receptor binding organic compound, and a cell surface receptor binding drug. Additional cell surface receptor ligands include, but are not limited to, cytokines, growth factors, hormones, antibodies, and angiogenic factors. In some embodiments, any art-recognized cell surface receptor ligand that can bind to a rare cell, e.g., a circulating tumor cell, a fetal cell, a stem cell and/or a microbe, can be used as a target-binding molecule on the magnetic particles described herein.

Microbe-binding Magnetic Particles

In some embodiments, the target-binding magnetic particles are adapted to specifically bind at least one or more microbes or fragments thereof (referred to as "microbe-binding magnetic particles") or microbe-associated molecular patterns (MAMPs), which are molecules or molecular motifs associated with microbes. An exemplary MAMP includes, but is not limited to, lipopolysaccharide (LPS) or an endotoxin.

The microbe-binding magnetic particles comprise on their surface microbe-binding molecules. A microbe-binding molecule can comprise at least one (e.g., one, two, three, four, five, six, seven, eight, nine, ten, eleven, twelve, thirteen, fourteen, fifteen, sixteen, seventeen, eighteen, nineteen, twenty or more) microbe surface-binding domain ("microbe binding domain"). The term "microbe surface-binding domain" as used herein refers to any molecules or a fragment thereof that can specifically bind to the surface of a microbe, e.g., any component present on a surface of a microbe, or a MAMP.

Any molecule or material that can bind to a microbe or MAMP can be employed as the microbe-binding molecule. Materials or substances which can serve as microbe-binding molecules include, for example, peptides, polypeptides, proteins, peptidomimetics, antibodies, antibody fragments (e.g., antigen binding fragments of antibodies), carbohydrate-binding protein, e.g., a lectin, glycoproteins, glycoprotein-binding molecules, amino acids, carbohydrates (including mono-, di-, tri- and poly-saccharides), lipids, steroids, hormones, lipid-binding molecules, cofactors, nucleosides, nucleotides, nucleic acids (e.g., DNA or RNA, analogues and derivatives of nucleic acids, or aptamers), peptidoglycan, lipopolysaccharide, small molecules, and any combinations thereof. The microbe-binding molecule can be covalently (e.g., cross-linked) or non-covalently linked to the magnetic particles.

In some embodiments, the microbe-binding molecule can comprise an opsonin or a fragment thereof. The term "opsonin" as used herein refers to naturally-occurring and synthetic molecules which are capable of binding to or attaching to the surface of a microbe or a pathogen, of acting as binding enhancers for a process of phagocytosis. Examples of opsonins which can be used in the engineered molecules described herein include, but are not limited to, vitronectin, fibronectin, complement components such as C1q (including any of its component polypeptide chains A, B and C), complement fragments such as C3d, C3b and C4b, mannose-binding protein, conglutinin, surfactant proteins A and D, C-reactive protein (CRP), alpha2-macroglobulin, and immunoglobulins, for example, the Fc portion of an immunoglobulin.

In some embodiments, the microbe-binding molecule comprises a carbohydrate recognition domain or a carbohydrate recognition portion thereof. As used herein, the term "carbohydrate recognition domain" refers to a region, at least a portion of which, can bind to carbohydrates on a surface of a microbe (e.g., a pathogen) or a MAMP.

In some embodiments, the microbe-binding molecule comprises at least a microbial-binding portion of C-type lectins, collectins, ficolins, receptor-based lectins, lectins from the shrimp *Marsupenaeus japonicas*, non-C-type lectins, lipopolysaccharide (LPS)-binding proteins, endotoxin-binding proteins, peptidoglycan-binding proteins, or any combinations thereof. In some embodiments, the microbe-binding molecules is selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), or any combinations thereof.

In some embodiments, the microbe-binding molecule comprises a lectin or a carbohydrate recognition or binding fragment or portion thereof. The term "lectin" as used herein refers to any molecules including proteins, natural or genetically modified, that interact specifically with saccharides (i.e., carbohydrates). The term "lectin" as used herein can also refer to lectins derived from any species, including, but not limited to, plants, animals, insects and microorganisms, having a desired carbohydrate binding specificity. Examples of plant lectins include, but are not limited to, the Leguminosae lectin family, such as ConA, soybean agglutinin, peanut lectin, lentil lectin, and *Galanthus nivalis* agglutinin (GNA) from the *Galanthus* (snowdrop) plant. Other examples of plant lectins are the Gramineae and Solanaceae families of lectins. Examples of animal lectins include, but are not limited to, any known lectin of the major groups S-type lectins, C-type lectins, P-type lectins, and I-type lectins, and galectins. In some embodiments, the carbohydrate recognition domain can be derived from a C-type lectin, or a fragment thereof. C-type lectin can include any carbohydrate-binding protein that requires calcium for binding. In some embodiments, the C-type lectin can include, but are not limited to, collectin, DC-SIGN, and fragments thereof. Without wishing to be bound by theory, DC-SIGN can generally bind various microbes by recognizing high-mannose-containing glycoproteins on their envelopes and/or function as a receptor for several viruses such as HIV and Hepatitis C.

In some embodiments, the microbe-binding molecules can comprise a microbe-binding portion of the C-type lectins, including, e.g., but not limited to, soluble factors such as Collectins (e.g., MBL, surfactant protein A, surfactant protein D and Collectin 11), ficolins (e.g. L-Ficolin, Ficolin A), receptor based lectins (e.g., DC-SIGN, DC-SIGNR, SIGNR1, Macrophage Mannose Receptor 1, Dectin-1 and Dectin-2), lectins from the shrimp *Marsupenaeus japonicus* (e.g., Lectin A, Lectin B and Lectin C), or any combinations thereof.

In some embodiments, the microbe-binding molecules can comprise at least a portion of non-C-type lectins (e.g., but not limited to, Wheat Germ Agglutinin).

In some embodiments, the microbe-binding molecules can comprise at least a portion of lipopolysaccharide (LPS)-binding proteins and/or endotoxin binding proteins (e.g., but not limited to, CD14, MD2, lipopolysaccharide binding proteins (LBP), limulus anti-LPS factor (LAL-F), or any combinations thereof).

In some embodiments, the microbe-binding molecules can comprise at least a portion of peptidoglycan binding proteins (e.g., but not limited to, mammalian peptidoglycan recognition protein-1 (PGRP-1), PGRP-2, PGRP-3, PGRP-4, or any combinations thereof.

In some embodiments, the microbe-binding molecules comprise the full amino acid sequence of a carbohydrate-binding protein, e.g., a lectin molecule. In some embodiments, the microbe-binding molecules are genetically engineered to remove a domain that activates the complement system and/or binds In some embodiments, the microbe-binding molecule comprises a mannose-binding lectin (MBL) or a carbohydrate binding fragment or portion thereof. Mannose-binding lectin, also called mannose binding protein (MBP), is a calcium-dependent serum protein that can play a role in the innate immune response by binding to carbohydrates on the surface of a wide range of microbes or pathogens (viruses, bacteria, fungi, protozoa) where it can activate the complement system. MBL can also serve as a direct opsonin and mediate binding and uptake of microbes or pathogens by tagging the surface of a microbe or pathogen to facilitate recognition and ingestion by phagocytes. Full length MBL and an engineered form of MBL (FcMBL and AKT-FcMBL) are described in the International Application Publication Nos. WO/2011/090954 and WO/2013/012924, contents of both of which are incorporated herein by reference.

Without wishing to be bound by a theory, microbe binding molecules comprising lectins or modified versions thereof can act as broad-spectrum microbe binding molecules (e.g., pathogen binding molecules). Accordingly, the method utilizing lectins (e.g., MBL and genetically engineered version of MBL (FcMBL and Akt-FcMBL)) as broad-spectrum microbe binding molecules (e.g., pathogen binding molecules) to capture microbes or MAMPs, can be carried out without identifying the microbe (e.g., pathogen).

In some embodiments, at least two (e.g. two, three, four, five, six, seven or more) microbe binding molecules can be linked together to form a multimeric microbe-binding molecule.

Any art-recognized recombinant carbohydrate-binding proteins or carbohydrate recognition domains can also be used in the microbe-binding molecules. For example, recombinant mannose-binding lectins, e.g., but not limited to, the ones disclosed in the U.S. Pat. Nos. 5,270,199; 6,846,649; and U.S. Patent Application No. US 2004/0,229,212, content of both of which is incorporated herein by reference, can be used in constructing a microbe-binding molecule.

In some embodiments, microbe-binding molecules and microbe-binding magnetic particles described in the International Application Publication Nos. WO/2011/090954 and WO/2013/012924, contents of both of which are incorporated herein by reference, can be used in the method described herein. For example, in some embodiments, the microbe-binding molecules can be selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof, as described in the International Application Publication Nos. WO/2011/090954 and WO/2013/012924, contents of both of which are incorporated herein by reference.

In some embodiments, the microbe-binding molecules each comprise an amino acid sequence selected from SEQ ID NO. 1-SEQ ID NO. 8, wherein the amino acid sequences are shown as follows:

```
MBL full length (SEQ ID NO. 1):
MSLFPSLPLL LLSMVAASYS ETVTCEDAQK

TCPAVIACSS PGINGFPGKD GRDGTKGEKG EPGQGLRGLQ GPPGKLGPPG

NPGPSGSPGP KGQKGDPGKS PDGDSSLAAS ERKALQTEMA RIKKWLTFSL

GKQVGNKFFL TNGEIMTFEK VKALCVKFQA SVATPRNAAE NGAIQNLIKE

EAFLGITDEK TEGQFVDLTG NRLTYTNWNE GEPNNAGSDE DCVLLLKNGQ

WNDVPCSTSH LAVCEFPI

MBL without the signal sequence (SEQ ID NO. 2):
ETVTCEDAQK TCPAVIACSS

PGINGFPGKD GRDGTKGEKG EPGQGLRGLQ GPPGKLGPPG NPGPSGSPGP

KGQKGDPGKS PDGDSSLAAS ERKALQTEMA RIKKWLTFSL GKQVGNKFFL

TNGEIMTFEK VKALCVKFQA SVATPRNAAE NGAIQNLIKE EAFLGITDEK

TEGQFVDLTG NRLTYTNWNE GEPNNAGSDE DCVLLLKNGQ WNDVPCSTSH

LAVCEFPI

Truncated MBL (SEQ ID NO. 3):
AASERKALQT EMARIKKWLT FSLGKQVGNK

FFLTNGEIMT FEKVKALCVK FQASVATPRN AAENGAIQNL IKEEAFLGIT

DEKTEGQFVD LTGNRLTYTN WNEGEPNNAG SDEDCVLLLK NGQWNDVPCS
```

```
TSHLAVCEFP I

Carbohydrate recognition domain (CRD) of MBL (SEQ ID NO. 4):
VGNKFFLTNG

EIMTFEKVKA LCVKFQASVA TPRNAAENGA IQNLIKEEAF LGITDEKTEG

QFVDLTGNRL TYTNWNEGEP NNAGSDEDCV LLLKNGQWND VPCSTSHLAV CEFPI

Neck + Carbohydrate recognition domain of MBL (SEQ ID NO. 5):
PDGDSSLAAS

ERKALQTEMA RIKKWLTFSL GKQVGNKFFL TNGEIMTFEK VKALCVKFQA

SVATPRNAAE NGAIQNLIKE EAFLGITDEK TEGQFVDLTG NRLTYTNWNE

GEPNNAGSDE DCVLLLKNGQ WNDVPCSTSH LAVCEFPI

FcMBL.81 (SEQ ID NO. 6):
EPKSSDKTHT CPPCPAPELL GGPSVFLFPP

KPKDTLMISR TPEVTCVVVD VSHEDPEVKFNWYVDGVEVH NAKTKPREEQ

YNSTYRVVSV LTVLHQDWLN GKEYKCKVSN KALPAPIEKT ISKAKGQPRE

PQVYTLPPSR DELTKNQVSL TCLVKGFYPS DIAVEWESNG

QPENNYKTTPPVLDSDGSFF LYSKLTVDKS RWQQGNVFSC SVMHEALHNH

YTQKSLSLSP GAPDGDSSLAASERKALQTE MARIKKWLTF SLGKQVGNKF

FLTNGEIMTF EKVKALCVKF QASVATPRNA AENGAIQNLI KEEAFLGITD

EKTEGQFVDL TGNRLTYTNW NEGEPNNAGS DEDCVLLLKN GQWNDVPCST

SHLAVCEFPI

Akt-FcMBL (SEQ ID NO. 7):
AKTEPKSSDKTHT CPPCPAPELL GGPSVFLFPP

KPKDTLMISR TPEVTCVVVD VSHEDPEVKF NWYVDGVEVH NAKTKPREEQ

YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP

GAPDGDSSLA ASERKALQTE MARIKKWLTF SLGKQVGNKF FLTNGEIMTF

EKVKALCVKF QASVATPRNA AENGAIQNLI KEEAFLGITD EKTEGQFVDL

TGNRLTYTNW NEGEPNNAGS DEDCVLLLKN GQWNDVPCST SHLAVCEFPI

FcMBL.111 (SEQ ID NO. 8):
EPKSSDKTHT CPPCPAPELL GGPSVFLFPP

KPKDTLMISR TPEVTCVVVD VSHEDPEVKF NWYVDGVEVH NAKTKPREEQ

YNSTYRVVSV LTVLHQDWLN GKEYKCKVSN KALPAPIEKT ISKAKGQPRE

PQVYTLPPSR DELTKNQVSL TCLVKGFYPS DIAVEWESNG QPENNYKTTP

PVLDSDGSFF LYSKLTVDKS RWQQGNVFSC SVMHEALHNH YTQKSLSLSP

GATSKQVGNKF FLTNGEIMTF EKVKALCVKF QASVATPRNA AENGAIQNLI

KEEAFLGITD EKTEGQFVDL TGNRLTYTNW NEGEPNNAGS DEDCVLLLKN

GQWNDVPCST SHLAVCEFPI
```

The microbe-binding molecules can contain sequences from the same species or from different species. For example, an interspecies hybrid microbe-binding molecule can contain a linker, e.g., a peptide linker, from a murine species, and a human sequence from a carbohydrate recognition domain protein, provided that they do not provide unacceptable levels of deleterious effects. The engineered microbe-binding molecules described herein can also include those that are made entirely from murine-derived sequences or fully human.

In some embodiments, the microbe-binding molecule can be linked to the C-terminal of a linker, e.g., a peptide linker. An exemplary peptide linker includes, but is not limited to, an Fc portion of an immunoglobulin.

General methods of preparing such microbe-binding molecules are well known in the art (Ashkenazi, A. and S. M. Chamow (1997), "Immunoadhesins as research tools and therapeutic agents," Curr. Opin. Immunol. 9(2): 195-200, Chamow, S. M. and A. Ashkenazi (1996). "Immunoadhesins: principles and applications," Trends Biotechnol. 14(2):52-60). In one example, an engineered microbe-binding molecule can be made by cloning into an expression vector such as Fc-X vector as discussed in Lo et al. (1998) 11:495 and PCT application no. PCT/US2011/021603, filed Jan. 19, 2011, content of both of which is incorporated herein by reference.

Target Molecules or Target Species to be Captured or Removed by the Methods, Kits, Devices, and Solid Substrates Described Herein The methods, devices, kits and solid substrates described herein can be used to capture, separate, or isolate one or more target molecules or species from a test sample. As used interchangeably herein, the term "target species" or "target molecules" refers to any molecule, cell or particulate that is to be separated or isolated from a fluid sample. Representative examples of target cellular species include, but are not limited to, mammalian cells, viruses, bacteria, fungi, yeast, protozoan, microbes, and parasites. Representative examples of target molecules include, but are not limited to, hormones, growth factors, cytokines (e.g., inflammatory cytokines), proteins, peptides, prions, lectins, oligonucleotides, carbohydrates, lipids, exosomes, contaminating molecules and particles, molecular and chemical toxins, and MAMPs. The target species can also include contaminants found in non-biological fluids, such as pathogens or lead in water or in petroleum products. Parasites can include organisms within the phyla Protozoa, Platyhelminthes, Aschelminthes, Acanthocephala, and Arthropoda.

In some embodiments, the target species can include a biological cell selected from the group consisting of living or dead cells (prokaryotic and eukaryotic, including mammalian), viruses, bacteria, fungi, yeast, protozoan, microbes, and parasites. The biological cell can be a normal cell or a diseased cell, e.g., a cancer cell. Mammalian cells include, without limitation; primate, human and a cell from any animal of interest, including without limitation; mouse, hamster, rabbit, dog, cat, domestic animals, such as equine, bovine, murine, ovine, canine, and feline. In some embodiments, the cells can be derived from a human subject. In other embodiments, the cells are derived from a domesticated animal, e.g., a dog or a cat. Exemplary mammalian cells include, but are not limited to, stem cells, cancer cells, progenitor cells, immune cells, blood cells, fetal cells, and any combinations thereof. The cells can be derived from a wide variety of tissue types without limitation such as; hematopoietic, neural, mesenchymal, cutaneous, mucosal, stromal, muscle, spleen, reticuloendothelial, epithelial, endothelial, hepatic, kidney, gastrointestinal, pulmonary, cardiovascular, T-cells, and fetus. Stem cells, embryonic stem (ES) cells, ES-derived cells, induced pluripotent stem cells, and stem cell progenitors are also included, including without limitation, hematopoietic, neural, stromal, muscle, cardiovascular, hepatic, pulmonary, and gastrointestinal stem cells. Yeast cells may also be used as cells in some embodiments described herein. In some embodiments, the cells can be ex vivo or cultured cells, e.g. in vitro. For example, for ex vivo cells, cells can be obtained from a subject, where the subject is healthy and/or affected with a disease. While cells can be obtained from a fluid sample, e.g., a blood sample, cells can also be obtained, as a non-limiting example, by biopsy or other surgical means know to those skilled in the art.

In some embodiments, the target molecules to be captured or removed from a fluid by the method described herein comprise microbes. As used herein, the term "microbes" generally refer to microorganisms, including bacteria, fungi, protozoan, archaea, protists, e.g., algae, and a combination thereof. The term "microbes" also includes pathogenic microbes, e.g., bacteria causing diseases such as plague, tuberculosis and anthrax; protozoa causing diseases such as malaria, sleeping sickness and toxoplasmosis; fungi causing diseases such as ringworm, candidiasis or histoplasmosis; and bacteria causing diseases such as sepsis. The term "microbe" or "microbes" can also encompass non-pathogenic microbes, e.g., some microbes used in industrial applications.

In some embodiments, the term "microbe" or "microbes" encompasses intact microbes and fragments of microbes, e.g., cell components of microbes, and MAMPs, e.g., lipopolysaccharide (LPS), and/or endotoxin.

Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii* (or *Pneumocystis carinii*), *Stachybotrys chartarum*, and any combination thereof.

Exemplary bacteria include, but are not limited to: anthrax, *campylobacter*, cholera, diphtheria, enterotoxigenic *E. coli*, giardia, gonococcus, *Helicobacter pylori*, Hemophilus influenza B, Hemophilus influenza non-typable, meningococcus, pertussis, pneumococcus, *salmonella, shigella, Streptococcus* B, group A *Streptococcus*, tetanus, *Vibrio cholerae, yersinia, Staphylococcus, Pseudomonas* species, Clostridia species, Myocobacterium tuberculosis, *Mycobacterium leprae, Listeria monocytogenes, Salmonella typhi, Shigella dysenteriae, Yersinia pestis, Brucella* species, *Legionella pneumophila*, Rickettsiae, *Chlamydia, Clostridium perfringens, Clostridium botulinum, Staphylococcus aureus, Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis, Neisseria meningitides*, and any combination thereof.

Exemplary parasites include, but are not limited to: *Entamoeba histolytica; Plasmodium* species, *Leishmania* species, Toxoplasmosis, Helminths, and any combination thereof.

Exemplary viruses include, but are not limited to, HIV-1, HIV-2, hepatitis viruses (including hepatitis B and C), Ebola virus, West Nile virus, and herpes virus such as HSV-2, adenovirus, dengue serotypes 1 to 4, ebola, enterovirus, herpes simplex virus 1 or 2, influenza, Japanese equine encephalitis, Norwalk, papilloma virus, parvovirus B19, rubella, rubeola, vaccinia, varicella, Cytomegalovirus, Epstein-Barr virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Human T-cell Leukemia virus type-1, Hantavirus, Rubella virus, Simian Immunodeficiency viruses, and any combination thereof.

In some embodiments, the method described herein can be used to capture, separate, or remove bioterror agents (e.g., B. *Anthracis*, and smallpox) from a fluid.

Exemplary contaminants found in non-biological fluids can include, but are not limited to microorganisms (e.g., *Cryptosporidium, Giardia lamblia*, bacteria, *Legionella*, Coliforms, viruses, fungi), bromates, chlorites, haloactic acids, trihalomethanes, chloramines, chlorine, chlorine dioxide, antimony, arsenic, mercury (inorganic), nitrates, nitrites, selenium, thallium, Acrylamide, Alachlor, Atrazine, Benzene, Benzo(a)pyrene (PAHs), Carbofuran, Carbon, etrachloride, Chlordane, Chlorobenzene, 2,4-D, Dalapon, 1,2-Dibromo-3-chloropropane (DBCP), o-Dichlorobenzene, p-Dichlorobenzene, 1,2-Dichloroethane, 1,1-Dichloroethylene, cis-1,2-Dichloroethylene, trans-1,2-Dichloroethylene, Dichloromethane, 1,2-Dichloropropane, Di(2-ethylhexyl) adipate, Di(2-ethylhexyl) phthalate, Dinoseb, Dioxin (2,3, 7,8-TCDD), Diquat, Endothall, Endrin, Epichlorohydrin, Ethylbenzene, Ethylene dibromide, Glyphosate, Heptachlor, Heptachlor epoxide, Hexachlorobenzene, Hexachlorocyclopentadiene, Lead, Lindane, Methoxychlor, Oxamyl (Vydate), Polychlorinated, biphenyls (PCBs), Pentachlorophenol, Picloram, Simazine, Styrene, Tetrachloroethylene, Toluene, Toxaphene, 2,4,5-TP (Silvex), 1,2,4-Trichlorobenzene, 1,1,1-Trichloroethane, 1,1,2-Trichloroethane, Trichloroethylene, Vinyl chloride, and Xylenes.

In some embodiments, the target species refers to a rare cell or a cellular component thereof. In some embodiments, the target species can refer to a rare cell or a cellular component thereof derived from a mammalian subject, including, without limitation, primate, human or any animal of interest such as mouse, hamster, rabbit, dog, cat, domestic animals, such as equine, bovine, murine, ovine, canine, and feline. In some embodiments, the rare cells can be derived from a human subject. In other embodiments, the rare cells can be derived from a domesticated animal or a pet such as a cat or a dog. As used herein, the term "rare cells" is defined, in some embodiments, as cells that are not normally present in a fluid sample, e.g., a biological fluid sample, but can be present as an indicator of an abnormal condition, such as infectious disease, chronic disease, injury, proliferative diseases, or pregnancy. In some embodiments, the term "rare cells" as used herein refers to cells that can be normally present in biological specimens, but are present with a frequency several orders of magnitude (e.g., at least about 100-fold, at least about 1000-fold, at least about 10000-fold) less than other cells typically present in a normal biological specimen. In some embodiments, rare cells are found infrequently in circulating blood, e.g., less than 100 cells (including less than 10 cells, less than 1 cell) per $10^8$ mononuclear cells in about 50 mL of peripheral blood. In some embodiments, a rare cell can be a normal cell or a diseased cell. Examples of rare cells include, but are not limited to, circulating tumor cells, progenitor cells, e.g., collected for bone marrow transplantation, blood vessel-forming progenitor cells, stem cells, circulating fetal cells, e.g., in maternal peripheral blood for prenatal diagnosis, virally-infected cells, cell subsets collected and manipulated for cell and gene therapy, and cell subpopulations purified for subsequent gene expression or proteomic analysis, other cells related to disease progression, and any combinations thereof.

As used herein, the term "a cellular component" in reference to circulating tumor cells, stem cells, fetal cells and/or microbes is intended to include any component of a cell that can be at least partially isolated from the cell, e.g., upon lysis of the cell. Cellular components can include, but are not limited to, organelles, such as nuclei, perinuclear compartments, nuclear membranes, mitochondria, chloroplasts, or cell membranes; polymers or molecular complexes, such as lipids, polysaccharides, proteins (membrane, trans-membrane, or cytosolic); nucleic acids, viral particles, or ribosomes; or other molecules, such as hormones, ions, and cofactors.

As used herein, the term "cytokine" can refer to any small cell-signaling protein molecule that is secreted by a cell of any type. Cytokines can include proteins, peptides, and/or glycoproteins. Based on their function, cell of secretion, and/or target of action, cytokines can be generally classified as lymphokines, interleukins, and chemokines. The term "lymphokines" as used herein generally refers to a subset of cytokines that are produced by a type of immune cell known as a lymphocyte. The term "interleukins" as used herein generally refers to cytokines secreted and/or synthesized by leukocytes and helper CD4+T lymphocytes, and/or through monocytes, macrophages, and/or endothelial cells. In some embodiments, interleukins can be human interleukins including IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, and IL-35. The term "chemokine" as used herein generally refers to a specific class of cytokines that mediates chemoattraction (chemotaxis) between cells. Examples of chemokines include, but are not limited to, CCL family, CXCL family, CX3CL family and XCL family.

The term "inflammatory cytokine" as used herein generally includes, without limitation, a cytokine that stimulates an inflammatory response. Examples of inflammatory cytokines include, without limitation, IFN-γ, IL-1, and TNF-α.

As used herein, the term "hormone" can refer to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; estradiol; androgens such as calusterone, dromostanolone propionate, epitiostanol, mepitiostane, or testolactone; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, gonadotropin-releasing hormone; inhibin; activin; mullerian-inhibiting substance; and thrombopoietin. As used herein, the term hormone includes proteins from natural sources or from recombinant cell culture and biologically active equivalents of the native-sequence hormone, including synthetically produced small-molecule entities and pharmaceutically acceptable derivatives and salts thereof.

The term "growth factor" as used herein can refer to proteins that generally promote growth, and include, for example, hepatic growth factor; fibroblast growth factor; vascular endothelial growth factor; nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, -β, and -γ; and colony stimulating factors (CSFs) such as macrophage-CSF (M-CSF); granulocyte-macrophage-CSF (GM-CSF); and granulocyte-CSF (G-CSF). As used herein, the term growth factor includes proteins from natural sources or from recombinant cell culture and biologically active equivalents of the native-sequence growth factor, including synthetically produced small-molecule entities and pharmaceutically acceptable derivatives and salts thereof.

As used herein, the term "molecular toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. Toxins include, but are not limited to, bacterial toxins, such as cholera toxin, heat-liable and heat-stable toxins of *E. coli*, toxins A and B of *Clostridium difficile*, aerolysins, and hemolysins; toxins produced by protozoa, such as *Giardia*; toxins produced by fungi. Molecular toxins can also include exotoxins, i.e., toxins secreted by an organism as an extracellular product, and enterotoxins, i.e., toxins present in the gut of an organism.

Example Applications and Fluid Suitable for the Methods, Kits, Devices, and Compositions Described Herein The methods, kits, devices, and solid substrates described herein are versatile and can be adapted to capture, separate, or remove any target molecules from any fluid, depending on the desired application of interest. Thus, fluids of any sources can be brought into contact with a magnetic capture surface as described herein or introduced into a magnetic separation chamber as described herein. For example, the fluid can be a biological fluid obtained or derived from a subject, a fluid or specimen obtained from an environmental source, a fluid from a cell culture, a microbe colony, or any combinations thereof.

In one embodiment, the methods, kits, devices, and solid substrates described herein can be used to capture, separate, or remove cells (including, e.g., rare cells such as circulating tumor cells or microbes) from a fluid of a subject and/or analyze the captured cells for therapeutic and/or diagnostic applications. Accordingly, in some embodiments, the fluid is a biological fluid selected from blood, plasma, cord blood, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof.

In some embodiments, the methods, kits, devices, and solid substrates described herein can be used to remove microbes and/or MAMPs from a fluid (e.g., blood or cord blood) of a subject or to purify a fluid (e.g., blood or cord blood) of a subject prior to preservation (e.g., cryopreservation) and/or transplantation. For example, one of the challenges in cryopreservation of cord blood is that 5-7% of cord blood samples are contaminated by pathogens (mostly *E. coli*), which potentially cause adverse effects on stem cells preserved in cord blood. Thus, treating cord blood to remove pathogenic contaminants using the method described herein is a beneficial step prior to a cryopreservation process.

In some embodiments, the methods, kits, devices, and solid substrates described herein can be used for continuous separation of cells or biomolecules from blood in an extracorporeal setup. For example, the methods, kits, devices, and solid substrates described herein can be used in blood dialysis of blood to remove microbes and/or toxins.

In some embodiments, the methods, kits, devices, and solid substrates described herein can be used to purify or clean a non-body or non-biological fluid, e.g., to remove target molecules from the non-body fluid. For example, the methods, kits, devices, and solid substrates described herein can be adapted to purify food products and water, e.g., to remove microbes, toxins, chemicals, and combinations thereof, in a continuous or batch process. Another example is to capture microbes and/or toxins from food, medium from microbial cultures (e.g., pharmaceutical manufacturing, beer brewing, etc.), water, or any other fluid. Accordingly, in some embodiments, the fluid is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, beer brewing, or any combinations thereof.

As used herein, the term "non-biological fluid" refers to any fluid that is not a biological fluid as the term is defined herein. Exemplary non-biological fluids include, but are not limited to, water, salt water, brine, buffered solutions, saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied samples), and mixtures thereof.

In some embodiments, the fluid can include a fluid (e.g., culture medium) from a biological culture. Examples of a fluid (e.g., culture medium) obtained from a biological culture includes the one obtained from culturing or fermentation, for example, of single- or multi-cell organisms, including prokaryotes (e.g., bacteria) and eukaryotes (e.g., animal cells, plant cells, yeasts, fungi), and including fractions thereof. In some embodiments, the fluid can include a fluid from a blood culture. In some embodiments, the culture medium can be obtained from any source, e.g., without limitations, research laboratories, pharmaceutical manufacturing plants, hydrocultures (e.g., hydroponic food farms), diagnostic testing facilities, clinical settings, and any combinations thereof.

The fluid, including any fluid or specimen (processed or unprocessed) can be liquid, supercritical fluid, solutions, suspensions, gases, gels, slurries, and combinations thereof. The fluid can be aqueous or non-aqueous. In some embodiments, the fluid can be an aqueous fluid. As used herein, the term "aqueous fluid" refers to any flowable water-containing material that is suspected of comprising a pathogen.

In some embodiments, the fluid can include a media or reagent solution used in a laboratory or clinical setting, such as for biomedical and molecular biology applications. As used herein, the term "media" refers to a medium for maintaining a tissue, an organism, or a cell population, or refers to a medium for culturing a tissue, an organism, or a cell population, which contains nutrients that maintain viability of the tissue, organism, or cell population, and support proliferation and growth.

As used herein, the term "reagent" refers to any solution used in a laboratory or clinical setting for biomedical and molecular biology applications. Reagents include, but are not limited to, saline solutions, PBS solutions, buffered solutions, such as phosphate buffers, EDTA, Tris solutions, and any combinations thereof. Reagent solutions can be used to create other reagent solutions. For example, Tris solutions and EDTA solutions are combined in specific ratios to create "TE" reagents for use in molecular biology applications.

In some embodiments, the methods, kits, devices, and solid substrates described herein are used to remove sepsis related target components from the blood of a subject in need thereof. As used herein, sepsis related target components refer to any molecule or bioparticle that can contribute to development of sepsis in a subject.

As used herein, "sepsis" refers to a body or subject's response to a systemic microbial infection. Sepsis is the leading cause of death of immunocompromised patients, and is responsible for over 200,000 deaths per year in the United States. The onset of sepsis occurs when rapidly growing infectious agents saturate the blood and overcome a subject's immunological clearance mechanisms. Most existing therapies are ineffective, and subjects can die because of clot formation, hypoperfusion, shock, and multiple organ failure.

In some embodiments, the methods, kits, devices, and solid substrates described herein are used to in combination with conventional therapies for treating a subject in need thereof. For example, the methods, kits, devices, and solid substrates described herein are used in conjunction with conventional therapies for sepsis treatment, such as fungicides. In another example, the methods, kits, devices, and solid substrates described herein are used for treating a subject having a cancer. In some embodiments, the methods, kits, devices, and solid substrates described herein can be used to remove cancer cells from a biological fluid obtained from the subject, and to provide an additional treatment including, but not limited to, chemotherapy, radiation therapy, steroids, bone marrow transplants, stem cell transplants, growth factor administration, ATRA (all-trans-retinoic acid) administration, histamine dihydrochloride (Ceplene) administration, interleukin-2 (Proleukin) administration, gemtuzumab ozogamicin (Mylotarg) administration, clofarabine administration, farnesyl transferase inhibitor administration, decitabine administration, inhibitor of MDR1 (multidrug-resistance protein) administration, arsenic trioxide administration, rituximab administration, cytarabine (ara-C) administration, anthracycline administration (such as daunorubicin or idarubicin), imatinib administration, dasatanib administration, nilotinib administration, purine analogue (such as fludarabine) administration, alemtuzumab (anti-CD52) administration, (fludarabine with cyclophosphamide), fludarabine administration, cyclophosphamide administration, doxorubicin administration, vincristine administration, prednisolone administration, lenalidomide administration, flavopiridol administration, or any combination therein. In some embodiments, the methods, kits, devices, and solid substrates described herein are used for treating a subject in need thereof without providing any other therapy to the subject. For example, the methods, kits, devices, and solid substrates described herein are used for sepsis treatment, pathogen and/or toxin clearance from biological fluids, of a subject in need thereof.

In some embodiments, the methods, kits, devices, and solid substrates described herein are used to purify or enrich a target component from a source fluid. For example, the methods, kits, devices, and solid substrates described herein can be used to purify products of chemical reactions or molecules being produced in a cell culture.

Solid Substrates

A solid substrate comprising a surface having magnetic field gradient concentrating particles distributed thereon and substantially aligned along magnetic flux lines of a magnetic field is also described herein. The solid substrate further comprises a target-binding magnetic particle and a target.

In one embodiment, the target is bound to the target-binding magnetic particle.

In some embodiments, the solid substrate is selected from the group consisting of a channel, a microfluidic channel, a sample well, a microtiter plate, a magnetic comb, a slide (e.g., a glass slide), a flask (e.g., a tissue culture flask), a tube, a nanotube, a fiber, a filter, a membrane, a scaffold, an extracorporeal device, a mixer, a microfluidic device, a hollow fiber, or any combinations thereof.

In some embodiments, the solid substrate can further comprise a structure or device that produces a magnetic field. Thus, the magnetic field gradient concentrating particles can be substantially aligned along magnetic flux lines of the magnetic field produced by the structure or device.

In some embodiments, the solid substrate can include a magnet embedded therein. For example, a magnetic multi-well tip comb contains a magnet in each tip. See, e.g., FIG. 6A.

In some embodiments, a magnet is placed in contact with or in proximity to at least one surface of the solid substrate. Accordingly, a system comprising (a) a magnet; and (b) the solid substrate described herein (comprising the magnetic field gradient concentrating particles, the target-binding magnetic particles and the target) is also described herein.

Kits

Another aspect described herein relates to a kit comprising (i) a device comprising a magnetic separation chamber or a magnetic capture surface; (ii) one or more containers containing magnetic field gradient concentrating particles; and (iii) one or more containers containing target-binding magnetic particles.

In some embodiments, the device can further comprise a structure or module that produces a magnetic field. In some embodiments, the structure or module that produces a magnetic field can be detachable from at least a portion of the device, e.g., the magnetic separation chamber or a magnetic capture surface.

The device comprising a magnetic separation chamber or a magnetic capture surface can be any fluid container or fluid processing device. For example, the device can be an eppendorf tube, a multi-well plate, a flask (e.g., a tissue culture flask), an extracorporeal device, a mixer, a hollow fiber cartridge, a microfluidic device, or any combinations thereof.

In some embodiments, the device is a microfluidic device. In one embodiment, the device can be an organ-on-chip device (e.g., a biospleen device).

In some embodiments, the device is a multi-well plate (e.g., 96-well plate).

Generation of Target-binding Magnetic Particles

The target-binding magnetic particles can be generated by attaching target-binding molecules to magnetic particles using any methods known in the art.

In some embodiments, the target-binding molecules can be attached the magnetic particles via a linker, which is described in detail below. In some embodiments, the linker can be a peptide linker. An exemplary peptide linker comprises an Fc portion of an immunoglobulin. In some embodiments, the N-terminus of the linker can comprise an amino acid sequence of AKT (alanine, lysine, threonine).

In some embodiments, the surface of the magnetic particles can be functionalized to include a coupling molecule for conjugation of the target-binding molecules. As used herein, the term "coupling molecule" refers to any molecule or any functional group that is capable of selectively binding with a microbe surface-binding domain. Representative examples of coupling molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The coupling molecules need not comprise an entire naturally occurring molecule but may consist of only a portion, fragment or subunit of a naturally or non-naturally occurring molecule, as for example the Fab fragment of an antibody. The coupling molecule can further comprise a detectable label. The coupling molecule can also encompass various functional groups that can couple the substrate to the engineered microbe surface-binding domains. Examples of such functional groups include, but are not limited to, an amino group, a carboxylic acid group, an epoxy group, and a tosyl group.

The coupling molecule can be conjugated to the surface of magnetic particles covalently or non-covalently using any of the methods known to those of skill in the art. For example, covalent immobilization can be accomplished through, for example, silane coupling. See, e.g., Weetall, 15 Adv. Mol. Cell Bio. 161 (2008); Weetall, 44 Meths. Enzymol. 134 (1976). The covalent interaction between the coupling molecule and the surface can also be mediated by other art-recognized chemical reactions, such as NHS reaction. The non-covalent interaction between the coupling molecule and the surface can be formed based on ionic interactions, van der Waals interactions, dipole-dipole interactions, hydrogen bonds, electrostatic interactions, and/or shape recognition interactions.

In certain embodiments, the organic moiety or functional groups can be surface functional groups capable of direct coupling of magnetic particles to target-binding molecules of a user's choice. For example, in some embodiments, the magnetic particles can be functionalized with various surface functional groups, e.g., amino groups, carboxylic acid groups, epoxy groups, tosyl groups, or silica-like groups. Suitable magnetic particles are commercially available such as from PerSeptive Diagnostics, Inc. (Cambridge, Mass.); Invitrogen Corp. (Carlsbad, Calif.); Cortex Biochem Inc. (San Leandro, Calif.); and Bangs Laboratories (Fishers, Ind.).

In alternative embodiments, the target-binding molecules can be conjugated to the surface of the magnetic particles by a coupling molecule pair. The term "coupling molecule pair" as used herein refers to the first and second molecules that specifically bind to each other. One member of the binding pair is conjugated to a magnetic particle while the second member is conjugated to a target-binding molecule. As used herein, the phrase "first and second molecules that specifically bind to each other" refers to binding of the first member of the coupling pair to the second member of the coupling pair with greater affinity and specificity than to other molecules. Exemplary coupling molecule pairs include, without limitations, any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin), hormone (e.g., thyroxine and cortisol-hormone binding protein), receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes). The coupling molecule pair can also include a first molecule that is negatively charged and a second molecule that is positively charged.

One non-limiting example of using conjugation with a coupling molecule pair is the biotin-sandwich method. See, e.g., Davis et al., 103 PNAS 8155 (2006). The two molecules to be conjugated together are biotinylated and then conjugated together using tetravalent streptavidin. In addition, a peptide can be coupled to the 15-amino acid sequence of an acceptor peptide for biotinylation (referred to as AP; Chen et al., 2 Nat. Methods 99 (2005)). The acceptor peptide sequence allows site-specific biotinylation by the E. Coli enzyme biotin ligase (BirA; Id.). An engineered microbe surface-binding domain can be similarly biotinylated for conjugation with a solid substrate. Many commercial kits are also available for biotinylating proteins. Another example for conjugation to a magnetic particle would be to use PLP-mediated bioconjugation. See, e.g., Witus et al., 132 JACS 16812 (2010). As described earlier, an AKT sequence on the N terminal of a linker, wherein the C-terminal of the linker is conjugated to a target-binding molecule, can allow the target-binding molecule to be biotinylated at a single site and further conjugated to a streptavidin-coated magnetic particle.

Linkers

As used herein, the term "linker" generally refers to a molecular entity that can directly or indirectly connect two parts of a composition, e.g., at least one target-binding molecule and a magnetic particle.

Linkers can be configures according to a specific need, e.g., based on at least one of the following characteristics. By way of example only, in some embodiments, linkers can be configured to have a sufficient length and flexibility such that it can allow for a target-binding molecule to orient accordingly with respect to a target molecule surface. In some embodiments, linkers can be configured to allow multimerization of at least two target-binding molecules (e.g., to from a di-, tri-, tetra-, penta-, or higher multimeric complex) while retaining biological activity (e.g., microbe-binding activity). In some embodiments, linkers can be configured to facilitate expression and purification of the target-binding molecule described herein. In some embodiments, linkers can be configured to provide at least one recognition-site for proteases or nucleases. In addition, linkers should be non-reactive with the functional components of the engineered molecule described herein (e.g., minimal hydrophobic or charged character to react with the functional protein domains such as a target-binding molecule).

In some embodiments, a linker can be configured to have any length in a form of a peptide, a protein, a nucleic acid (e.g., DNA or RNA), or any combinations thereof. In some embodiments, the peptide or nucleic acid linker can vary from about 1 to about 1000 amino acids long, from about 10 to about 500 amino acids long, from about 30 to about 300 amino acids long, or from about 50 to about 150 amino acids long. Longer or shorter linker sequences can be also used for the target-binding molecule described herein. In one embodiment, the peptide linker has an amino acid sequence of about 200 to 300 amino acids in length.

In some embodiments, a peptide or nucleic acid linker can be configured to have a sequence comprising at least one of the amino acids selected from the group consisting of glycine (Gly), serine (Ser), asparagine (Asn), threonine (Thr), methionine (Met) or alanine (Ala), or at least one of codon sequences encoding the aforementioned amino acids (i.e., Gly, Ser, Asn, Thr, Met or Ala). Such amino acids and corresponding nucleic acid sequences are generally used to provide flexibility of a linker. However, in some embodiments, other uncharged polar amino acids (e.g., Gln, Cys or Tyr), nonpolar amino acids (e.g., Val, Leu, Ile, Pro, Phe, and Trp), or nucleic acid sequences encoding the amino acids thereof can also be included in a linker sequence. In alternative embodiments, polar amino acids or nucleic acid sequence thereof can be added to modulate the flexibility of a linker. One of skill in the art can control flexibility of a linker by varying the types and numbers of residues in the linker. See, e.g., Perham, 30 Biochem. 8501 (1991); Wriggers et al., 80 Biopolymers 736 (2005).

In alternative embodiments, a linker can be a chemical linker of any length. In some embodiments, chemical linkers can comprise a direct bond or an atom such as oxygen or sulfur, a unit such as NH, C(O), C(O)NH, SO, SO2, SO2NH, or a chain of atoms, such as substituted or unsubstituted C1-C6 alkyl, substituted or unsubstituted C2-C6 alkenyl, substituted or unsubstituted C2-C6 alkynyl, substituted or unsubstituted C6-C12 aryl, substituted or unsubstituted C5-C12 heteroaryl, substituted or unsubstituted C5-C12 heterocyclyl, substituted or unsubstituted C3-C12 cycloalkyl, where one or more methylenes can be interrupted or terminated by O, S, S(O), SO2, NH, or C(O). In some embodiments, the chemical linker can be a polymer chain (branched or linear).

In some embodiments where the linker is a peptide, such peptide linker can comprise at least a portion of an immunoglobulin, e.g., IgA, IgD, IgE, IgG and IgM including their subclasses (e.g., IgG1), or a modified thereof. In some embodiments, the peptide linker can comprise a portion of fragment crystallization (Fc) region of an immunoglobulin or a modified thereof. In such embodiments, the portion of the Fc region that can be used as a linker can comprise at least one region selected from the group consisting of a hinge region, a CH2 region, a CH3 region, and any combinations thereof. By way of example, in some embodiments, a CH2 region can be excluded from the portion of the Fc region as a linker. In one embodiment, Fc linker comprises a hinge region, a CH2 domain and a CH3 domain. Such Fc linker can be used to facilitate expression and purification of the target-binding molecule described herein. The N terminal Fc has been shown to improve expression levels, protein folding and secretion of the fusion partner. In addition, the Fc has a staphylococcal protein A binding site, which can be used for one-step purification protein A affinity chromatography. See Lo K M et al. (1998) Protein Eng. 11: 495-500. Further, such Fc linker have a molecule weight above a renal threshold of about 45 kDa, thus reducing the possibility of target-binding molecule being removed by glomerular filtration. Additionally, the Fc linker can allow dimerization of two target-binding molecule to form a dimer, e.g., a dimeric MBL molecule.

In various embodiments, the N-terminus or the C-terminus of the linker, e.g., the portion of the Fc region, can be modified. By way of example only, the N-terminus or the C-terminus of the linker can be extended by at least one additional linker described herein, e.g., to provide further flexibility, or to attach additional molecules. In some embodiments, the N-terminus of the linker can be linked directly or indirectly (via an additional linker) with a substrate-binding domain adapted for orienting the carbohydrate recognition domain away from the substrate. Exemplary Fc linked MBL (FcMBL and Akt-FcMBL) are described in PCT application no. PCT/US2011/021603, filed Jan. 19, 2011, content of which is incorporated herein by reference.

In some embodiments, the linkers can be branched. For branched linkers, the linker can link at least one (e.g., one, two, three, four, five, six, seven, eight, nine, ten or more) target-binding molecule(s) to a magnetic particle.

In some embodiments, the C-terminal of the linker can be conjugated to a target-binding molecule.

Embodiments of Various Aspects Described Herein can be Defined in any of the Following Numbered Paragraphs:

1. A method of capturing at least one target from a fluid comprising:
   introducing a fluid and target-binding magnetic particles to a magnetic separation chamber in the presence of a magnetic field gradient (a gradient of a magnetic field), wherein at least a portion of a fluid-contact surface of the magnetic separation chamber comprises magnetic field gradient concentrating particles distributed thereon and substantially aligned along magnetic flux lines of the magnetic field, and
   wherein the magnetic field gradient concentrating particles act as local magnetic field gradient concentrators and attracts at least a portion of the target-binding magnetic particles to the magnetic field gradient concentrating particles in the presence of the magnetic field gradient, whereby a target bound on the target-binding magnetic particles is captured from the fluid.
2. The method of paragraph 1, wherein the magnetic field gradient concentrating particles form magnetic micro- or nano-structures on said at least a portion of the fluid-contact surface of the magnetic separation chamber.
3. The method of paragraph 1 or 2, wherein the magnetic field gradient concentrating particles comprise superparamagnetic particles, paramagnetic particles, ferrimagnetic particles, ferromagnetic particles, or combinations thereof.
4. The method of any of paragraphs 1-3, wherein the magnetic field gradient concentrating particles are ferromagnetic particles.
5. The method of paragraph 4, wherein the ferromagnetic particles are particles of reduced iron, atomized iron, electrolyte iron, nickel, cobalt, permalloy, alloy comprising at least one or a combination of two or more aforementioned ferromagnetic materials, compounds of rare earth metals, minerals (e.g., iodestone), or a combination of two or more thereof.
6. The method of any of paragraphs 1-5, wherein the diameter of the target-binding magnetic particles is no more than 250 nm, no more than 100 nm, no more than 50 nm, or no more than 5 nm.
7. The method of any of paragraphs 1-6, wherein the diameter of the magnetic field gradient concentrating particles ranges from about 50 nm to about 5 mm.
8. The method of paragraph 7, wherein the diameter of the magnetic field gradient concentrating particles is about 300 μm.
9. The method of any of paragraphs 1-8, wherein at least 50% area or higher of said at least a portion of the fluid-contact surface comprises the magnetic field gradient concentrating particles distributed thereon.
10. The method of any of paragraphs 1-9 wherein efficiency of magnetically capturing the target-bound targeting-binding magnetic particles from the fluid is increased by at least about 50% (including, e.g., at least about 60%, at least about 70%, at least about 80%, at least about 90%)

or more, as compared to the efficiency in the absence of the magnetic field concentrating particles.
11. The method of any of paragraphs 1-10, wherein efficiency of magnetically capturing the target-bound targeting-binding magnetic particles from the fluid is increased by at least about 1.1-fold (including, e.g., at least about 1.5-fold, at least about 2-fold, at least about 3-fold, at least about 4-fold) or more, as compared to the efficiency in the absence of the magnetic field concentrating particles.
12. The method of any of paragraphs 1-11, wherein the fluid is flowed through the magnetic separation chamber at a flow rate of about 1 ml/hr to about 10 L/hr.
13. The method of any of paragraphs 1-12, wherein the magnetic separation chamber comprises a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a hollow fiber, or any combinations thereof.
14. The method of any of paragraphs 1-13, wherein the fluid is a biological fluid obtained or derived from a subject, a fluid or specimen obtained from an environmental source, a fluid from a cell culture, a microbe colony, or any combinations thereof.
15. The method of paragraph 14, wherein the fluid is a biological fluid selected from blood, plasma, cord blood, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof.
16. The method of paragraph 14, wherein the fluid is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, beer brewing, or any combinations thereof.
17. The method of any of paragraphs 1-16, wherein the target-binding magnetic particles are paramagnetic or superparamagnetic particles.
18. The method of any of paragraphs 1-17, wherein the target-binding magnetic particles are magnetic particles adapted to bind a target selected from the group consisting of cells, proteins, nucleic acids, microbes, small molecules, chemicals, toxins, drugs, and combinations thereof.
19. The method of any of paragraphs 1-18, wherein the target-binding magnetic particles are microbe-binding magnetic particles.
20. The method of paragraph 19, wherein the microbe-binding magnetic particles comprise on their surface microbe-binding molecules.
21. The method of paragraph 20, wherein the microbe-binding molecule is selected from the group consisting of opsonins, lectins, antibodies and antigen binding fragments thereof, proteins, peptides, peptidomimetics, carbohydrate-binding proteins, nucleic acids, carbohydrates, lipids, steroids, hormones, lipid-binding molecules, cofactors, nucleosides, nucleotides, nucleic acids, peptidoglycan, lipopolysaccharide-binding proteins, small molecules, and any combination thereof.
22. The method of paragraph 20 or 21, wherein the microbe-binding molecule comprises at least a microbial-binding portion of C-type lectins, collectins, ficolins, receptor-based lectins, lectins from the shrimp *Marsupenaeus japonicas*, non-C-type lectins, lipopolysaccharide (LPS)-binding proteins, endotoxin-binding proteins, peptidoglycan-binding proteins, or any combinations thereof.
23. The method of any of paragraphs 20-22, wherein the microbe-binding molecule is selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), or any combinations thereof.
24. The method of any of paragraphs 20-23, wherein the microbe-binding molecules are attached to the microbe-binding magnetic particles via a linker.
25. The method of paragraph 24, wherein the N-terminus of the linker comprises an amino acid sequence of AKT (alanine, lysine, threonine).
26. The method of paragraph 24 or 25, wherein the linker is a peptide linker.
27. The method of any of paragraphs 24-26, wherein the linker comprises a Fc portion of an immunoglobulin.
28. The method of any of paragraphs 20-27, wherein the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.
29. The method of any of paragraphs 20-28, wherein the microbe-binding molecule comprises an amino acid sequence selected from SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and any combination thereof.
30. A kit comprising (i) a device comprising a magnetic separation surface or chamber; (ii) one or more containers containing magnetic field gradient concentrating particles; and (iii) one or more containers containing target-binding magnetic particles.
31. The kit of paragraph 30, wherein the device is a microfluidic device (e.g., a biospleen device).
32. The kit of paragraph 30 or 31, wherein the magnetic field gradient concentrating particles comprise superparamagnetic particles, paramagnetic particles, ferrimagnetic particles, ferromagnetic particles, and combinations thereof.
33. The kit of any of paragraphs 30-32, wherein the magnetic field gradient concentrating particles are ferromagnetic particles.
34. The kit of any of paragraphs 30-33, wherein the target-binding magnetic particles are magnetic particles adapted or funcationalized to bind a target selected from the group consisting of cells, proteins, nucleic acids, microbes, small molecules, chemicals, toxins, drugs, and combinations thereof.
35. The kit of any of paragraphs 30-34, wherein the target-binding magnetic particles are microbe-binding magnetic particles.

36. The kit of any of paragraphs 30-35, wherein the diameter of the target-binding magnetic particles is no more than 250 nm, no more than 100 nm, no more than 50 nm, or no more than 5 nm.

37. The kit of any of paragraphs 30-36, wherein the diameter of the magnetic field gradient concentrating particles ranges from about 50 nm to about 5 mm.

38. A solid substrate comprising (i) a surface having magnetic field gradient concentrating particles distributed thereon and substantially aligned along magnetic flux lines of a magnetic field; (ii) target-binding magnetic particles; and (iii) a target.

39. The solid substrate of paragraph 38, wherein the target is bound to at least one of the target-binding magnetic particles.

40. The solid substrate of paragraph 38 or 39, wherein the diameter of the magnetic field gradient concentrating particles ranges from about 50 nm to about 5 mm.

41. The solid substrate of any of paragraphs 38-40, wherein the diameter of the target-binding magnetic particles is no more than 250 nm, no more than 100 nm, no more than 50 nm, or no more than 5 nm.

42. The solid substrate of any of paragraphs 38-41, wherein the magnetic field gradient concentrating particles comprise superparamagnetic particles, paramagnetic particles, ferrimagnetic particles, ferromagnetic particles, and combinations thereof.

43. The solid substrate of any of paragraphs 38-42, wherein the magnetic field gradient concentrating particles are ferromagnetic particles.

44. The solid substrate of any of paragraphs 38-43, wherein the target is selected from the group consisting of cells, proteins, nucleic acids, microbes, small molecules, chemicals, toxins, drugs, and combinations thereof.

45. The solid substrate of any of paragraphs 38-44, wherein the solid substrate is selected from the group consisting of a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a microfluidic device, a hollow fiber, or any combinations thereof.

46. The solid substrate of any of paragraphs 38-45, wherein the target-binding magnetic particles are microbe-binding magnetic particles, and the target comprises a microbe.

47. The solid substrate of paragraph 46, wherein the microbe-binding magnetic particles comprise each on its surface microbe-binding molecules.

48. The solid substrate of paragraph 47, wherein the microbe-binding molecules are selected from the group consisting of opsonins, lectins, antibodies and antigen binding fragments thereof, proteins, peptides, peptidomimetics, carbohydrate-binding proteins, nucleic acids, carbohydrates, lipids, steroids, hormones, lipid-binding molecules, cofactors, nucleosides, nucleotides, nucleic acids, peptidoglycan, lipopolysaccharide-binding proteins, small molecules, and any combination thereof.

49. The solid substrate of paragraph 47 or 48, wherein the microbe-binding molecules each comprises at least a microbial-binding portion of C-type lectins, collectins, ficolins, receptor-based lectins, lectins from the shrimp *Marsupenaeus japonicas*, non-C-type lectins, lipopolysaccharide (LPS)-binding proteins, endotoxin-binding proteins, peptidoglycan-binding proteins, or any combinations thereof.

50. The solid substrate of any of paragraphs 47-49, wherein the microbe-binding molecules are each selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), or any combinations thereof.

51. The solid substrate of any of paragraphs 47-50, wherein the microbe-binding molecules are attached to the microbe-binding magnetic particles via a linker.

52. The solid substrate of paragraph 51, wherein the N-terminus of the linker comprises an amino acid sequence of AKT (alanine, lysine, threonine).

53. The solid substrate of paragraph 51 or 52, wherein the linker is a peptide linker.

54. The solid substrate of any of paragraphs 51-53, wherein the linker comprises a Fc portion of an immunoglobulin.

55. The solid substrate of any of paragraphs 47-54, wherein the microbe-binding molecules are each selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.

56. The solid substrate of any of paragraphs 47-55, wherein the microbe-binding molecule comprises an amino acid sequence selected from SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and any combination thereof.

57. A method of separating magnetic particles from a fluid comprising:
    subjecting a magnetic capture surface and magnetic field gradient concentrating particles to a magnetic field gradient (a gradient of a magnetic field), wherein the magnetic field gradient concentrating particles, in the presence of the magnetic field gradient, distribute on at least a portion of a magnetic capture surface and substantially align along magnetic flux lines of the magnetic field; and
    contacting the magnetic capture surface with a fluid comprising magnetic particles, wherein the magnetic field gradient concentrating particles act as local magnetic field gradient concentrators, thereby attracting at least a portion of the magnetic particles to the magnetic field gradient concentrating particles in the presence of the magnetic field gradient and separating the magnetic particles from the fluid.

58. The method of paragraph 57, wherein the magnetic field gradient concentrating particles form magnetic micro- or nano-structures on said at least a portion of the magnetic capture surface.

59. The method of paragraph 57 or 58, wherein the magnetic field gradient concentrating particles comprise superparamagnetic particles, paramagnetic particles, ferrimagnetic particles, ferromagnetic particles, or combinations thereof.

60. The method of any of paragraphs 57-59, wherein the magnetic field gradient concentrating particles are ferromagnetic particles.

61. The method of paragraph 60, wherein the ferromagnetic particles are particles of reduced iron, atomized iron, electrolyte iron, nickel, cobalt, permalloy, alloy comprising at least one or a combination of two or more aforementioned ferromagnetic materials, compounds of rare earth metals, minerals (e.g., iodestone), or a combination of two or more thereof.
62. The method of any of paragraphs 57-61, wherein a dimension (e.g., diameter) of the magnetic particles is no more than 250 nm, no more than 100 nm, no more than 50 nm, or no more than 5 nm.
63. The method of any of paragraphs 57-62, wherein a dimension (e.g., diameter) of the magnetic field gradient concentrating particles ranges from about 50 nm to about 5 mm.
64. The method of paragraph 63, wherein the dimension (e.g., diameter) of the magnetic field gradient concentrating particles is about 300 μm.
65. The method of any of paragraphs 57-64, wherein at least 50% area or higher of said at least a portion of the magnetic capture surface comprises the magnetic field gradient concentrating particles distributed thereon.
66. The method of any of paragraphs 57-65, wherein efficiency of separating the magnetic particles from the fluid is increased by at least about 50% (including, e.g., at least about 60%, at least about 70%, at least about 80%, at least about 90%) or more, as compared to the efficiency in the absence of the magnetic field concentrating particles.
67. The method of any of paragraphs 57-66, wherein efficiency of separating the magnetic particles from the fluid is increased by at least about 1.1-fold (including, e.g., at least about 1.5-fold, at least about 2-fold, at least about 3-fold, at least about 4-fold) or more, as compared to the efficiency in the absence of the magnetic field concentrating particles.
68. The method of any of paragraphs 57-67, wherein a local magnetic field gradient experienced by the magnetic particles is increased by at least about 30% or higher (including, e.g., at least about 40%, at least about 50%, at least about 60%, at least about 70%, at least about 80%, at least about 90%, or higher), as compared to that experienced by the magnetic particles in the absence of the magnetic field concentrating particles.
69. The method of any of paragraphs 57-68, wherein a local magnetic field gradient experienced by the magnetic particles is increased by at least about 1.1-fold or higher (including, e.g., at least about 1.5-fold, at least about 2-fold, at least about 3-fold, at least about 4-fold, at least about 5-fold, at least about 10-fold, at least about 50-fold, at least about 100-fold, at least about 150-fold or higher), as compared to that experienced by the magnetic particles in the absence of the magnetic field concentrating particles.
70. The method of any of paragraphs 57-69, wherein the magnetic capture surface forms at least part of a magnetic separation chamber.
71. The method of paragraph 70, wherein the magnetic separation chamber comprises or is a channel, a microfluidic channel, a sample well, a microtiter plate, a slide (e.g., a glass slide), a flask (e.g., a tissue culture flask), a tube, a nanotube, a fiber, a filter, a membrane, a scaffold, an extracorporeal device, a mixer, a hollow fiber, or any combinations thereof.
72. The method of any of paragraphs 57-67, wherein the fluid is flowed through the magnetic separation chamber at a flow rate of about 1 ml/hr to about 10 L/hr.
73. The method of any of paragraphs 57-72, wherein the fluid is a biological fluid obtained or derived from a subject, a fluid or specimen obtained or derived from an environmental source, a fluid from a cell culture, a microbe colony, or any combinations thereof.
74. The method of paragraph 73, wherein the fluid is a biological fluid selected from blood, plasma, cord blood, serum, lactation products, amniotic fluids, sputum, saliva, urine, semen, cerebrospinal fluid, bronchial aspirate, bronchial lavage aspirate fluid, perspiration, mucus, liquefied stool sample, synovial fluid, peritoneal fluid, pleural fluid, pericardial fluid, lymphatic fluid, tears, tracheal aspirate, a homogenate of a tissue specimen, or any mixtures thereof.
75. The method of paragraph 73, wherein the fluid is a fluid or specimen obtained from an environmental source selected from a fluid or specimen obtained or derived from food products, food produce, poultry, meat, fish, beverages, dairy product, water (including wastewater), ponds, rivers, reservoirs, swimming pools, soils, food processing and/or packaging plants, agricultural places, hydrocultures (including hydroponic food farms), pharmaceutical manufacturing plants, animal colony facilities, beer brewing, or any combinations thereof.
76. The method of any of paragraphs 57-75, wherein the magnetic particles are paramagnetic or superparamagnetic particles.
77. The method of any of paragraphs 57-76, wherein the magnetic particles are magnetic particles adapted or functionalized to bind a target selected from the group consisting of cells, proteins, nucleic acids, microbes, small molecules, chemicals, toxins, drugs, and combinations thereof.
78. The method of any of paragraphs 57-77, wherein the magnetic particles are microbe-binding magnetic particles.
79. The method of paragraph 78, wherein the microbe-binding magnetic particles comprise on their surface microbe-binding molecules.
80. The method of paragraph 79, wherein the microbe-binding molecule is selected from the group consisting of opsonins, lectins, antibodies and antigen binding fragments thereof, proteins, peptides, peptidomimetics, carbohydrate-binding proteins, nucleic acids, carbohydrates, lipids, steroids, hormones, lipid-binding molecules, cofactors, nucleosides, nucleotides, nucleic acids, peptidoglycan, lipopolysaccharide-binding proteins, small molecules, and any combination thereof.
81. The method of paragraph 79 or 80, wherein the microbe-binding molecule comprises at least a microbial-binding portion of C-type lectins, collectins, ficolins, receptor-based lectins, lectins from the shrimp *Marsupenaeus japonicas*, non-C-type lectins, lipopolysaccharide (LPS)-binding proteins, endotoxin-binding proteins, peptidoglycan-binding proteins, or any combinations thereof.
82. The method of any of paragraphs 79-81, wherein the microbe-binding molecule is selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), or any combinations thereof.
83. The method of any of paragraphs 78-82, wherein the microbe-binding molecules are attached to the microbe-binding magnetic particles via a linker.
84. The method of paragraph 83, wherein the N-terminus of the linker comprises an amino acid sequence of AKT (alanine, lysine, threonine).

85. The method of paragraph 83 or 84, wherein the linker is a peptide linker.
86. The method of any of paragraphs 83-85, wherein the linker comprises an Fc portion of an immunoglobulin.
87. The method of any of paragraphs 79-86, wherein the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.
88. The method of any of paragraphs 79-87, wherein the microbe-binding molecule comprises an amino acid sequence selected from SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and any combination thereof.
89. The method of any of paragraphs 77-88, wherein the method captures at least one target from the fluid.
90. A method of capturing at least one target from a fluid comprising:
    introducing a fluid comprising target-binding magnetic particles to a magnetic separation chamber in the presence of a magnetic field gradient (a gradient of a magnetic field), wherein at least a portion of a fluid-contact surface of the magnetic separation chamber comprises magnetic field gradient concentrating particles distributed thereon and aligned along with magnetic flux lines of the magnetic field,
    wherein the magnetic field gradient concentrating particles act as local magnetic field gradient concentrators, thereby attracting at least a portion of target-bound target-binding magnetic particles to the magnetic field gradient concentrating particles in the presence of the magnetic field gradient.
91. The method of paragraph 90, wherein the magnetic field gradient concentrating particles form magnetic micro- or nano-structures on said at least a portion of the fluid-contact surface of the magnetic separation chamber.
92. The method of paragraph 1, 57, or 90, wherein the magnetic field gradient concentrating particles are treated to reduce or inhibit non-specific interaction between the magnetic field gradient concentrating particles and said at least one target.
93. The paragraph of paragraph 92, wherein the magnetic field gradient concentrating particles are treated with a blocking agent.
94. The paragraph of paragraph 93, wherein the blocking agent comprises a lubricant (e.g., but not limited to silicone and/or mold-release agent), a polymer (e.g., but not limited to silicon-based polymer such as polydimethylsiloxane (PDMS)), milk proteins, bovine serum albumin, blood serum, whole blood, or a combination of two or more thereof.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%. When "0%" is used to describe the amount of a component, it is understood that this includes situations where only trace amounts of the component are present.

All patents, patent applications, and publications identified in this document are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples are not intended to limit the scope of the invention, but are rather intended to be exemplary of certain embodiments.

Example 1

Integration of Ferromagnetic Particles in a Microfluidic Device to Increase Throughput and/or Separation Efficiency of the Device This Example describes a method to increase magnetic separation efficiency of an organ-on-chip device (e.g., a biospleen device as described in the International Patent Application Nos. WO2012135834; WO 2011091037; and WO 2007044642, the contents of each of which are incorporated herein by reference) using ferromagnetic particles trapped in the channels or coating fluid-contact surface of the channels. The ferromagnetic particles-integrated in the organ-on-chip devices (e.g., a biospleen device) can be used for high-throughput cleansing of any fluid, e.g., blood, other biological fluids, water, food or any other liquid that can flow.

The method involves ferromagnetic beads distributed or magnetically trapped on fluid-contact surfaces of an organ-on-chip device (e.g., either in the saline channel and blood channel of the biospleen device). To do this, for example, the ferromagnetic particles (~10 mg to 500 mg) added to 10~50 mL of either buffer or ethanol were introduced using a peristaltic pump into the channel(s) of the organ-on-chip device (e.g., a biospleen device) where the magnet(s) were placed outside in proximity to the channel(s) of the organ-on-chip device to trap the ferromagnetic particles, e.g., onto the surface of the channel(s) while buffer or ethanol containing the ferromagnetic particles was continuously flowing through the channel(s) of the device. In some embodiments where a biospleen device (e.g., described in WO2012135834), the magnet(s) were placed on the top (e.g., the saline channel) or at the bottom (e.g., the blood channel) of the device to trap the ferromagnetic particles onto the surface of the channel.

Once the ferromagnetic particles were trapped inside the channel of the device, the magnet(s) were manipulated to distribute those ferromagnetic particles uniformly over the fluid-contact surface area of the channel. Once the ferromagnetic particles were dispersed, the magnets (e.g., permanent magnets) were located either on one or both sides of the device. For example, magnet(s) were placed on the top and/or at the bottom of the biospleen device.

When more than one magnets are placed facing each other, the magnets attract and pull each other. The ferromagnetic particles trapped inside the channels become magnetized (saturated with the magnetic flux) and aligned along the magnetic flex lines diverging from the magnets on one side (e.g., on the bottom) and converging toward the magnets on the opposing side (e.g., on the top). Because the ferromagnetic particles are aligned vertically along the magnetic flux lines, they do not clog the channels if, for example, less than <900 mg of ferromagnetic particles are loaded in a biospleen device.

Accordingly, different amount of the ferromagnetic particles (10 mg to 500 mg) were distributed or magnetically trapped on surface(s) of an organ-on-chip device (e.g., a biospleen device). The magnetic isolation efficiency was measured, for example, using microbes (e.g., *S. aureus*) captured by small microbe-binding magnetic particles (e.g., 50 nm FcMBL magnetic beads) at a flow rate of 2 L/h to correlate the amount of the ferromagnetic particles with the isolation efficiency. The ferromagnetic particles and the FcMBL magnetic beads were collected from the device after removing magnets from the devices.

Figure 2:
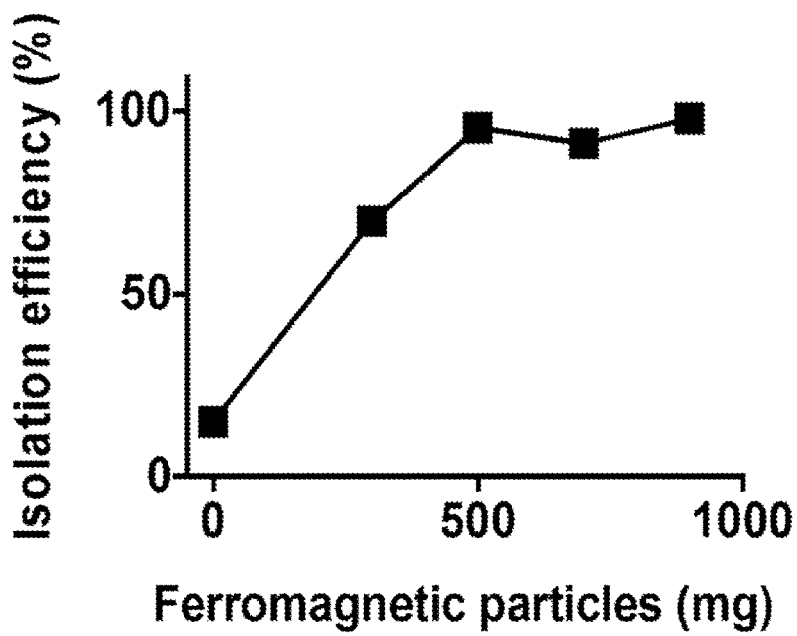
FIG. 2 is a line graph showing correlation of the magnetic isolation efficiency with different amounts of the ferromagnetic particles trapped in a microfluidic device (e.g., a biospleeen device). $S.$ $aureus$ ($10^4$ cfu/mL) bound with 128 nm FcMBL magnetic beads in TBST $Ca^{++}$ were flowed through a channel (e.g., of the biospleen device) primed with the ferromagnetic particles (300 mg~900 mg) at a flow rate of 2 L/h.
Figure 3:
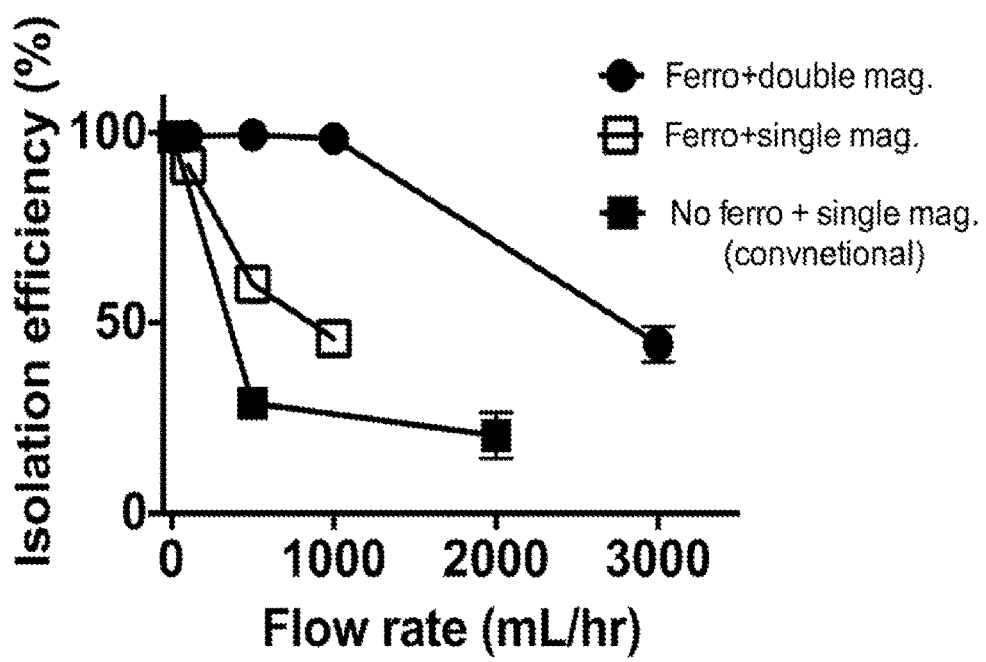
FIG. 3 is a line graph showing isolation efficiency of $S.$ $aureus$ prebound with 50 nm FcMBL magnetic beads in TBST buffer (10 mL) in a single round of magnetic separation using the methods described herein. The "biofluid" or "sample" channel (e.g., of the biospleen device) was primed with the ferromagnetic particles (500 mg) and the permanent magnets applied the magnetic fields from the top and bottom of the device, which greatly enhanced the magnetic forces acting on the 50 nm magnetic beads that have weak magnetic moment.

In some embodiments, different amount of the ferromagnetic particles (300 mg to 900 mg) were loaded in the biospleen device and the magnetic isolation efficiency of *S. aureus* bound with 128 nm FcMBL magnetic beads flowing at 2 L/h was measured. FIG. 2 shows that the isolation efficiency increased and plateaued at about 500 mg of the ferromagnetic particles. FIG. 3 shows that the ferromagnetic particles integrated in the biospleen device enabled separation of pathogens bound to 50 nm beads with over 99% efficiency at a flow rate of 1 L/h, which represents more than a five-fold increase in isolation efficiency compared to the biospleen device without the ferromagnetic particles.

The magnetic beads that captured target molecules (e.g., pathogens) and were trapped by or attracted to the ferromagnetic particles can be released from the ferromagnetic particles, for example, by pipetting or demagnetizing the ferromagnetic particles, e.g., with a demagnetizer. Therefore, the target molecules that bound to the magnetic beads can be subjected to subsequent analysis, such as ELISA or PCA, without interference from the ferromagnetic particles.

Example 2

Integration of Ferromagnetic Particles in a Microfluidic Device for Depletion of Microbes (e.g., Pathogens) from Cord Blood One of the challenges in cryopreservation of cord blood is that 5-7% of cord blood samples are contaminated by pathogens (mostly *E. coli*), which potentially cause adverse effects on stem cells preserved in cord blood. Thus, treating cord blood to remove pathogenic contaminants is a beneficial step prior to a cryopreservation process.

As a proof of concept, 3-6 cfu of *S. aureus* and *E. coli* (Bioball®) were spiked into 10 mL of cord blood. The pathogen-containing cord blood was mixed with FcMBL magnetic beads and then introduced into a ferromagnetic particle-integrated biospleen device (as described in Example 1) for 5 hours at a flow rate of 20 mL/h. The method to prime the biospleen device with ferromagnetic particles is the same as described in Example 1. Samples (250 uL) were taken at 0, 2, 4, and 5 hour-time points and then inoculated into blood culture vials, followed by 5-day culture at 37° C.

After 2-5 days of culture at 37° C., the blood culture vials was examined to determine if they turned turbid or remained clear. A turbid blood culture is indicative of at least one pathogen remained in the cord blood samples that has flown through the biospleen device. FIG. 4 shows that the pathogens initially spiked into the cord blood samples were successfully removed by the method described above, as evidenced by a clear blood culture even when the sample was treated with the ferromagnetic particles-integrated biospleen device for only 2 hours, whereas the control cord blood consistently contained pathogens over 5 hours. The control cord blood refers to cord blood flowing through a biospleen device without target-binding magnetic particles.

Example 3

Enhanced Magnetic Depletion Efficiency of Clinical Isolate Pathogens in Eppendorf Tubes, Combining 50 nm Microbe-binding Magnetic Beads and Ferromagnetic Beads One of the issues to address is to expand a range of microbes (e.g., pathogens) that bind FcMBL magnetic beads so that they can be detected either by ELISA or microfluidic devices. Smaller magnetic beads generally provide a higher binding efficiency. However, smaller beads generate weak magnetic forces; thus, the conventional methods are not capable of efficiently separate small magnetic beads from a fluid sample. The methods described herein provide enhanced magnetic force gradient for separating magnetic particles, including smaller magnetic particles that cannot be efficiently separated by the conventional magnetic separation methods, from a fluid sample. Thus, smaller magnetic particles can be used to bind target molecules with the methods described herein.

In this Example, the RS218 clinical isolate of *E. coli* was incubated with 50 nm FcMBL magnetic beads for 20 min in TBST $Ca^{++}$ 5 mM, and then ferromagnetic particles (10-500 mg) were added into the solution, followed by magnetic depletion using magnet(s).

Figure 5:
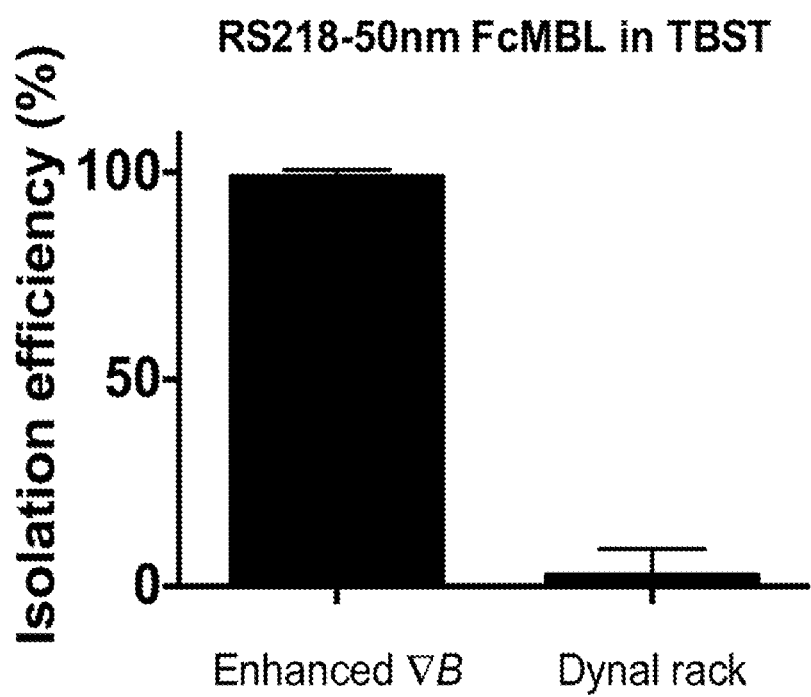
FIG. 5 is a bar graph showing RS218 *E. coli* depletion efficiency using 50 nm FcMBL magnetic beads and ferromagnetic particles. Because of highly enhanced magnetic flux density gradients generated by ferromagnetic beads, RS218 captured by 50 nm beads were efficiently removed whereas the conventional Dynal magnetic rack yielded less than 5% depletion efficiency.

FIG. 5 shows that the magnetic depletion assay without addition of ferromagnetic particles yielded about 30% magnetic isolation efficiency even in TBST $Ca^{++}$. However, with the addition of ferromagnetic particles into the solution, >99% magnetic depletion efficiency was achieved with RS218 captured by 50 nm FcMBL magnetic beads.

Example 4

Enhanced Magnetic Depletion Efficiency of Clinical Isolate Pathogens in 96-Well Plates Combining 50 nm Microbe-binding Magnetic Beads and Ferromagnetic Beads The multi-well plate platform provides a powerful technology that enables high throughput analysis of samples employing robotics and automation. While the conventional 96 well plate-based ELISA platform using target-binding magnetic beads (Kingfisher™ or BioTek Inc.) provides capability to detect multiple target molecules simultaneously, but the platform is not able to achieve high binding efficiency of smaller target-binding magnetic beads (e.g. 50 nm) due to their inherent weak magnetic force.

This Example shows distributing or dispersing ferromagnetic particles on a fluid-contact surface of a magnetic separation chamber significantly increase the capture efficiency of pathogens that have not been depleted by the conventional 96-well plate-based methods using the smaller microbe-binding magnetic particles alone (without ferromagnetic particles).

The RS218 clinical isolate of *E. coli* was incubated with 50 nm FcMBL magnetic beads for a period of time in TBST $Ca^{++}$ 5 mM. The ferromagnetic particles (e.g., about 10 mg to 500 mg by weight in total and the particles were approximately 300 µm in diameter) were first added to each well to form a ferromagnetic structure or layer, followed by the addition of the fluid sample comprising the RS128 and FcMBL magnetic beads. The mixture was then followed by magnetic depletion in different 96-well plate-based platform formats using magnet(s). FIG. 6A shows that the method described herein can be adapted for use in a 96-well deep well plate (e.g., from KingFisher®). The movable plate head has a 96-tip comb, where each tip of the comb holds and protects a magnet during the magnetic separation process. The ferromagnetic particles added in deep wells formed 2D or 3D nano- or micro-structure on the fluid-contact surface of the tip when the movable plate head (with the magnetic tip comb) was brought close to the deep wells. Incubating the RS218 clinical isolate sample comprising the FcMBL magnetic beads in the presence of the formed ferromagnetic structures yielded over 99% capture efficiency of RS218 *E. coli* bound with 50 nm FcMBL magnetic beads whereas no microbe depletion was observed when the plate was used without the ferromagnetic particles.

FIG. 6B shows that the method described herein can also be adapted for use in a 96-well conventional plate placed on a magnetic plate holder and a shaker. The ferromagnetic particles added in the wells formed 2D or 3D nano- or micro-structure at least at the bottom surface of the wells where the magnets are located. Shaking the RS218 clinical isolate sample comprising the FcMBL magnetic beads for about 20 min at 700 rpm in the presence of the formed ferromagnetic structures yielded over 99% capture efficiency of RS218 *E. coli* bound with 50 nm FcMBL magnetic beads whereas no microbe depletion was observed when the plate was used without the ferromagnetic particles.

FIG. 6C shows that the method described herein can also be adapted for use in a 96-well conventional plate placed on a magnetic plate holder and a rotating mixer. The ferromagnetic particles added in the wells formed 2D or 3D nano- or micro-structure at least at the bottom surface of the wells where the magnets are located. Rotating the RS218 clinical isolate sample comprising the FcMBL magnetic beads at 10 rpm in the presence of the formed ferromagnetic structures yielded over 99% capture efficiency of RS218 *E. coli* bound with 50 nm FcMBL magnetic beads whereas no microbe depletion was observed when the plate was used without the ferromagnetic particles.

Figure 6D:
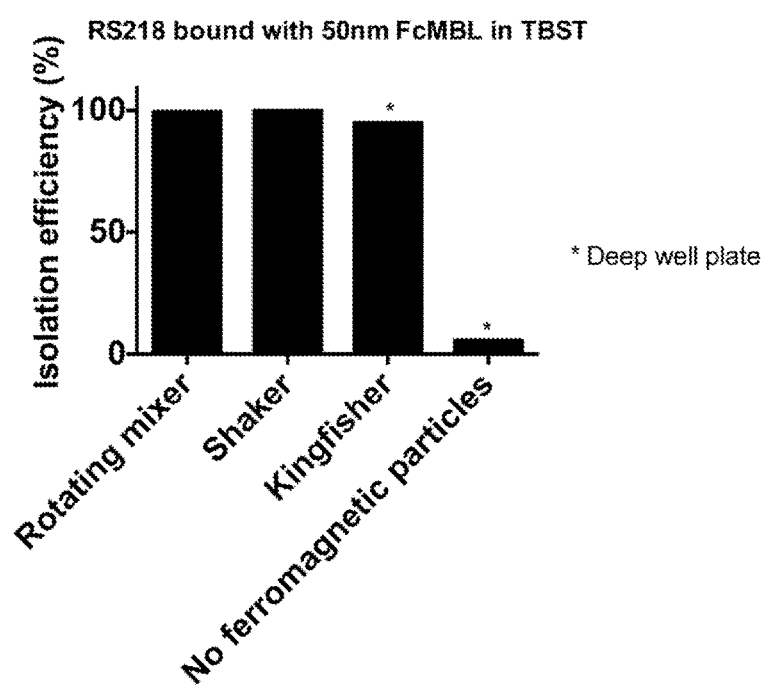

FIG. 6D shows the depletion efficiency of RS218 *E. coli* bound on 50 nm FcMBL magnetic beads using different 96-well plate platforms as shown in FIGS. 6A-6C with and without the ferromagnetic particles. All three different capture conditions yielded over 90% depletion efficiency of 50 nm bead bound RS218 *E. coli* when the ferromagnetic particles are present.

Example 5

Figure 7:
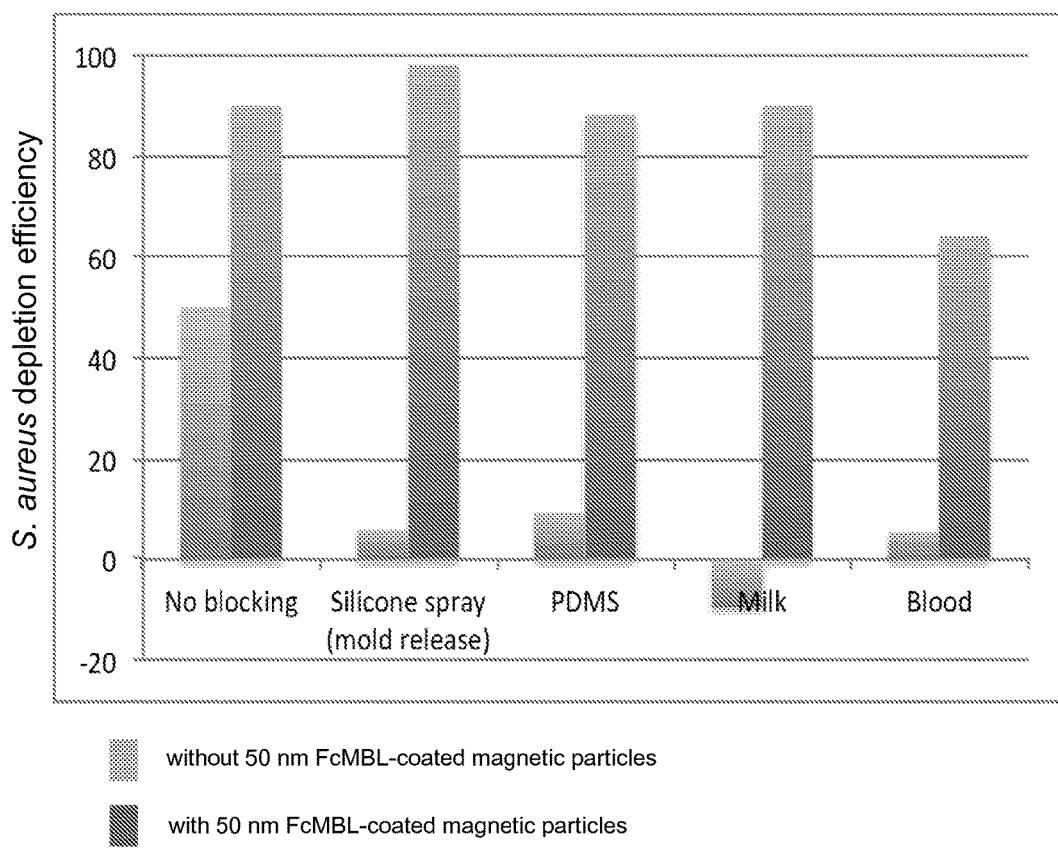
FIG. 7 is a bar graph showing depletion efficiency of *S. aureus* using FcMBL-coated magnetic particles captured by enhanced magnetic separation in the presence of ferromagnetic iron powder that has been treated with different blocking agents.

Improving Specificity of Magnetic Separation by Blocking Magnetic Field Gradient Concentrating Particles to Reduce Non-specific Interaction In some embodiments, the magnetic field gradient concentrating particles can have non-specific interaction with target molecule(s) to be captured, removed, or separated from a fluid. To reduce or inhibit such non-specific interaction, the magnetic field gradient concentrating particles can be pre-treated. By way of example only, ferromagnetic iron powder (as an example of the magnetic field gradient concentrating particles) has non-specific interaction with microbes or pathogens. In this Example, iron powder was treated with different blocking agents (e.g., but not limited to, mold-release agent such as silicone spray, PDMS, milk, and human whole blood) to evaluate effects of each blocking agent on pathogen depletion efficiency with or without target-binding magnetic particles (e.g., 50 nm FcMBL-coated magnetic particles). In some embodiments, iron powder was treated by contacting with different blocking agents for about 20 min (with mixing as desired). The iron powder, upon contact with a blocking agent, was then washed with an appropriate buffer (e.g., at least twice or more). The iron powder (e.g., about 0.5 g) treated with different blocking reagents was incubated with microbes of interest (e.g., *S. aureus*; $10^3$ CFU/mL) spiked in TBST buffer (without 50 nm FcMBL-coated magnetic particles), and the microbial depletion efficiency was then measured. FIG. 7 (data without FcMBL-coated magnetic particles) shows that the tested blocking reagents efficiently inhibited or reduced non-specific interaction between iron powder and microbes or pathogens.

The blocked iron powder was then used in combination with 50 nm FcMBL-coated magnetic particles to assess microbial depletion efficiency. For example, microbes or pathogens (e.g., *S. aureus*) in about 1 mL of TBST were first contacted with about 50 µL of 50 nm FcMBL-coated magnetic particles to allow the microbes to bind to the FcMBL-coated magnetic particles. The microbe-bound FcMBL-coated magnetic particles (e.g., *S. aureus*-bound FcMBL-coated magnetic particles) were then depleted or removed from the fluid or sample by magnetic field gradients enhanced by the addition of the blocked iron powder. FIG. 7 (data with FcMBL-coated magnetic particles) shows that most of the *S. aureus*-bound FcMBL-coated magnetic particles were depleted or removed from the fluid or sample by magnetic field gradients enhanced by the addition of the blocked iron powder.

This Example shows that selectivity of capturing or separating target molecules or cells from a fluid can be significantly improved by (i) reducing non-specific interaction between magnetic field gradient concentrating particles (e.g., iron powder) and target molecules to be removed (e.g., microbes), and (ii) using a selective target-binding magnetic particles to capture the target molecules. In some embodiments, the selective target-binding magnetic particles can be so small in size that they are not efficiently separated by a conventional magnetic separator, e.g., due to a too weak magnetic moment, because the methods, devices, kits, and/or solid substrates described herein provide high efficiency of magnetic separation, even using small target-binding magnetic particles.

An exemplary approach of reducing non-specific interaction between magnetic field gradient concentrating particles and target molecules to be removed can comprise treating the magnetic field gradient concentrating particles with a blocking agent. Examples of the blocking agent can include, but are not limited to, a lubricant (e.g., but not limited to silicone and/or mold-release agent), a polymer (e.g., but not limited to silicon-based polymer such as polydimethylsiloxane (PDMS)), milk proteins, bovine serum albumin, blood serum, whole blood, and a combination of two or more thereof.

---

What is claimed is:

1. A method of capturing at least one target from a fluid comprising:
introducing a fluid and target-binding magnetic particles to a magnetic separation chamber in the presence of a magnetic field gradient (a gradient of a magnetic field),
wherein at least a portion of a fluid-contact surface of the magnetic separation chamber comprises magnetic field gradient concentrating particles distributed thereon and substantially aligned along magnetic flux lines of the magnetic field,
wherein the magnetic field gradient concentrating particles act as local magnetic field gradient concentrators and attracts at least a portion of the target-binding magnetic particles to the magnetic field gradient concentrating particles in the presence of the magnetic field gradient, thereby capturing a target bound on the target-binding magnetic particles from the fluid,
wherein the target-binding magnetic particles are microbe-binding magnetic particles, and
wherein the microbe-binding magnetic particles comprise on their surface microbe-binding molecules, and
wherein the microbe-binding molecule is selected from the group consisting of opsonins and lectins.

2. The method of claim 1, wherein the magnetic field gradient concentrating particles form magnetic micro- or nano-structures on said at least a portion of the fluid-contact surface of the magnetic separation chamber.

3. The method of claim 1, wherein the diameter of the target-binding magnetic particles is no more than 250 nm.

4. The method of claim 1, wherein at least 50% area or higher of said at least a portion of the fluid-contact surface comprises the magnetic field gradient concentrating particles distributed thereon.

5. The method of claim 1, wherein the fluid is flowed through the magnetic separation chamber at a flow rate of about 1 ml/hr to about 10 L/hr.

6. The method of claim 1, wherein the magnetic separation chamber comprises a channel, a microfluidic channel, a sample well, a microtiter plate, a slide, a flask, a tube, a nanotube, a fiber, a filter, a membrane, a scaffold, an extracorporeal device, a mixer, a hollow fiber, or any combinations thereof.

7. The method of claim 1, wherein the fluid is a biological fluid obtained or derived from a subject, a fluid or specimen obtained from an environmental source, a fluid from a cell culture, a microbe colony, or any combinations thereof.

8. The method of claim 1, wherein the target-binding magnetic particles are paramagnetic or superparamagnetic particles.

9. The method of claim 1, wherein the microbe-binding molecule comprises at least a microbial-binding portion of C-type lectins, collectins, ficolins, receptor-based lectins, lectins from the shrimp Marsupenaeus japonicas, non-C-type lectins, lipopolysaccharide (LPS)-binding proteins, endotoxin-binding proteins, peptidoglycan-binding proteins, or any combinations thereof; or wherein the microbe-binding molecule is selected from the group consisting of mannose-binding lectin (MBL), surfactant protein A, surfactant protein D, collectin 11, L-ficolin, ficolin A, DC-SIGN, DC-SIGNR, SIGNR1, macrophage mannose receptor 1, dectin-1, dectin-2, lectin A, lectin B, lectin C, wheat germ agglutinin, CD14, MD2, lipopolysaccharide-binding protein (LBP), limulus anti-LPS factor (LAL-F), mammalian peptidoglycan recognition protein-1 (PGRP-1), PGRP-2, PGRP-3, PGRP-4, C-reactive protein (CRP), and any combinations thereof.

10. The method of claim 1, wherein the microbe-binding molecule is selected from the group consisting of MBL (mannose binding lectin), FcMBL (IgG Fc fused to mannose binding lectin), AKT-FcMBL (IgG Fc-fused to mannose binding lectin with the N-terminal amino acid tripeptide of sequence AKT (alanine, lysine, threonine)), and any combination thereof.

11. The method of claim 1, wherein the microbe-binding molecule comprises an amino acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, and any combination thereof.

12. A method of capturing at least one target from a fluid comprising:
introducing a fluid comprising target-binding magnetic particles to a magnetic separation chamber in the presence of a magnetic field gradient (a gradient of a magnetic field), wherein at least a portion of a fluid-contact surface of the magnetic separation chamber comprises magnetic field gradient concentrating particles distributed thereon and aligned along with magnetic flux lines of the magnetic field,
wherein the magnetic field gradient concentrating particles act as local magnetic field gradient concentrators, thereby attracting at least a portion of target-bound target-binding magnetic particles to the magnetic field gradient concentrating particles in the presence of the magnetic field gradient,
wherein the target-binding magnetic particles are microbe-binding magnetic particles,
wherein the microbe-binding magnetic particles comprise on their surface microbe-binding molecules, and
wherein the microbe-binding molecule is selected from the group consisting of opsonins and lectins.

* * * * *

SEQUENCE LISTING

<160> NUMBER OF SEQ ID NOS: 8

<210> SEQ ID NO 1
<211> LENGTH: 248
<212> TYPE: PRT
<213> ORGANISM: Homo sapiens

<400> SEQUENCE: 1

```
Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 2
<211> LENGTH: 228
<212> TYPE: PRT
<213> ORGANISM: Homo sapiens

<400> SEQUENCE: 2

Glu Thr Val Thr Cys Glu Asp Ala Gln Lys Thr Cys Pro Ala Val Ile
1               5                   10                  15

Ala Cys Ser Ser Pro Gly Ile Asn Gly Phe Pro Gly Lys Asp Gly Arg
            20                  25                  30

Asp Gly Thr Lys Gly Glu Lys Gly Glu Pro Gly Gln Gly Leu Arg Gly
        35                  40                  45

Leu Gln Gly Pro Pro Gly Lys Leu Gly Pro Pro Gly Asn Pro Gly Pro
    50                  55                  60

Ser Gly Ser Pro Gly Pro Lys Gly Gln Lys Gly Asp Pro Gly Lys Ser
65                  70                  75                  80

Pro Asp Gly Asp Ser Ser Leu Ala Ala Ser Glu Arg Lys Ala Leu Gln
                85                  90                  95

Thr Glu Met Ala Arg Ile Lys Lys Trp Leu Thr Phe Ser Leu Gly Lys
            100                 105                 110

Gln Val Gly Asn Lys Phe Phe Leu Thr Asn Gly Glu Ile Met Thr Phe
            115                 120                 125

Glu Lys Val Lys Ala Leu Cys Val Lys Phe Gln Ala Ser Val Ala Thr
130                 135                 140

Pro Arg Asn Ala Ala Glu Asn Gly Ala Ile Gln Asn Leu Ile Lys Glu
145                 150                 155                 160

Glu Ala Phe Leu Gly Ile Thr Asp Glu Lys Thr Glu Gly Gln Phe Val
                165                 170                 175

Asp Leu Thr Gly Asn Arg Leu Thr Tyr Thr Asn Trp Asn Glu Gly Glu
            180                 185                 190

Pro Asn Asn Ala Gly Ser Asp Glu Asp Cys Val Leu Leu Leu Lys Asn
        195                 200                 205

Gly Gln Trp Asn Asp Val Pro Cys Ser Thr Ser His Leu Ala Val Cys
    210                 215                 220

Glu Phe Pro Ile
225

<210> SEQ ID NO 3
<211> LENGTH: 141
<212> TYPE: PRT
<213> ORGANISM: Homo sapiens

<400> SEQUENCE: 3

Ala Ala Ser Glu Arg Lys Ala Leu Gln Thr Glu Met Ala Arg Ile Lys
1               5                   10                  15

Lys Trp Leu Thr Phe Ser Leu Gly Lys Gln Val Gly Asn Lys Phe Phe
            20                  25                  30

Leu Thr Asn Gly Glu Ile Met Thr Phe Glu Lys Val Lys Ala Leu Cys
        35                  40                  45

Val Lys Phe Gln Ala Ser Val Ala Thr Pro Arg Asn Ala Ala Glu Asn
    50                  55                  60

Gly Ala Ile Gln Asn Leu Ile Lys Glu Glu Ala Phe Leu Gly Ile Thr
65                  70                  75                  80

Asp Glu Lys Thr Glu Gly Gln Phe Val Asp Leu Thr Gly Asn Arg Leu
                85                  90                  95

Thr Tyr Thr Asn Trp Asn Glu Gly Glu Pro Asn Asn Ala Gly Ser Asp
            100                 105                 110

Glu Asp Cys Val Leu Leu Leu Lys Asn Gly Gln Trp Asn Asp Val Pro
            115                 120                 125

```
Cys Ser Thr Ser His Leu Ala Val Cys Glu Phe Pro Ile
        130                 135                 140

<210> SEQ ID NO 4
<211> LENGTH: 115
<212> TYPE: PRT
<213> ORGANISM: Homo sapiens

<400> SEQUENCE: 4

Val Gly Asn Lys Phe Phe Leu Thr Asn Gly Glu Ile Met Thr Phe Glu
  1               5                  10                  15

Lys Val Lys Ala Leu Cys Val Lys Phe Gln Ala Ser Val Ala Thr Pro
             20                  25                  30

Arg Asn Ala Ala Glu Asn Gly Ala Ile Gln Asn Leu Ile Lys Glu Glu
         35                  40                  45

Ala Phe Leu Gly Ile Thr Asp Glu Lys Thr Glu Gly Gln Phe Val Asp
     50                  55                  60

Leu Thr Gly Asn Arg Leu Thr Tyr Thr Asn Trp Asn Glu Gly Glu Pro
 65                  70                  75                  80

Asn Asn Ala Gly Ser Asp Glu Asp Cys Val Leu Leu Leu Lys Asn Gly
                 85                  90                  95

Gln Trp Asn Asp Val Pro Cys Ser Thr Ser His Leu Ala Val Cys Glu
            100                 105                 110

Phe Pro Ile
        115

<210> SEQ ID NO 5
<211> LENGTH: 148
<212> TYPE: PRT
<213> ORGANISM: Homo sapiens

<400> SEQUENCE: 5

Pro Asp Gly Asp Ser Ser Leu Ala Ala Ser Glu Arg Lys Ala Leu Gln
  1               5                  10                  15

Thr Glu Met Ala Arg Ile Lys Lys Trp Leu Thr Phe Ser Leu Gly Lys
             20                  25                  30

Gln Val Gly Asn Lys Phe Phe Leu Thr Asn Gly Glu Ile Met Thr Phe
         35                  40                  45

Glu Lys Val Lys Ala Leu Cys Val Lys Phe Gln Ala Ser Val Ala Thr
     50                  55                  60

Pro Arg Asn Ala Ala Glu Asn Gly Ala Ile Gln Asn Leu Ile Lys Glu
 65                  70                  75                  80

Glu Ala Phe Leu Gly Ile Thr Asp Glu Lys Thr Glu Gly Gln Phe Val
                 85                  90                  95

Asp Leu Thr Gly Asn Arg Leu Thr Tyr Thr Asn Trp Asn Glu Gly Glu
            100                 105                 110

Pro Asn Asn Ala Gly Ser Asp Glu Asp Cys Val Leu Leu Leu Lys Asn
            115                 120                 125

Gly Gln Trp Asn Asp Val Pro Cys Ser Thr Ser His Leu Ala Val Cys
            130                 135                 140

Glu Phe Pro Ile
145

<210> SEQ ID NO 6
<211> LENGTH: 380
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 6

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Ala Pro Asp Gly Asp Ser Ser Leu Ala
225                 230                 235                 240

Ala Ser Glu Arg Lys Ala Leu Gln Thr Glu Met Ala Arg Ile Lys Lys
                245                 250                 255

Trp Leu Thr Phe Ser Leu Gly Lys Gln Val Gly Asn Lys Phe Phe Leu
            260                 265                 270

Thr Asn Gly Glu Ile Met Thr Phe Glu Lys Val Lys Ala Leu Cys Val
        275                 280                 285

Lys Phe Gln Ala Ser Val Ala Thr Pro Arg Asn Ala Ala Glu Asn Gly
290                 295                 300

Ala Ile Gln Asn Leu Ile Lys Glu Glu Ala Phe Leu Gly Ile Thr Asp
305                 310                 315                 320

Glu Lys Thr Glu Gly Gln Phe Val Asp Leu Thr Gly Asn Arg Leu Thr
                325                 330                 335

Tyr Thr Asn Trp Asn Glu Gly Glu Pro Asn Asn Ala Gly Ser Asp Glu
            340                 345                 350

Asp Cys Val Leu Leu Leu Lys Asn Gly Gln Trp Asn Asp Val Pro Cys
        355                 360                 365

Ser Thr Ser His Leu Ala Val Cys Glu Phe Pro Ile
370                 375                 380
```

<210> SEQ ID NO 7
<211> LENGTH: 383
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Ala Lys Thr Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
    50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Ala Pro Asp Gly Asp Ser
225                 230                 235                 240

Ser Leu Ala Ala Ser Glu Arg Lys Ala Leu Gln Thr Glu Met Ala Arg
                245                 250                 255

Ile Lys Lys Trp Leu Thr Phe Ser Leu Gly Lys Gln Val Gly Asn Lys
            260                 265                 270

Phe Phe Leu Thr Asn Gly Glu Ile Met Thr Phe Glu Lys Val Lys Ala
        275                 280                 285

Leu Cys Val Lys Phe Gln Ala Ser Val Ala Thr Pro Arg Asn Ala Ala
    290                 295                 300

Glu Asn Gly Ala Ile Gln Asn Leu Ile Lys Glu Ala Phe Leu Gly
305                 310                 315                 320

Ile Thr Asp Glu Lys Thr Glu Gly Gln Phe Val Asp Leu Thr Gly Asn
                325                 330                 335

Arg Leu Thr Tyr Thr Asn Trp Asn Glu Gly Glu Pro Asn Asn Ala Gly
            340                 345                 350

Ser Asp Glu Asp Cys Val Leu Leu Leu Lys Asn Gly Gln Trp Asn Asp
        355                 360                 365
```

```
Val Pro Cys Ser Thr Ser His Leu Ala Val Cys Glu Phe Pro Ile
        370                 375                 380
```

<210> SEQ ID NO 8
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Ala Thr Ser Lys Gln Val Gly Asn Lys
225                 230                 235                 240

Phe Phe Leu Thr Asn Gly Glu Ile Met Thr Phe Glu Lys Val Lys Ala
                245                 250                 255

Leu Cys Val Lys Phe Gln Ala Ser Val Ala Thr Pro Arg Asn Ala Ala
            260                 265                 270

Glu Asn Gly Ala Ile Gln Asn Leu Ile Lys Glu Glu Ala Phe Leu Gly
        275                 280                 285

Ile Thr Asp Glu Lys Thr Glu Gly Gln Phe Val Asp Leu Thr Gly Asn
    290                 295                 300

Arg Leu Thr Tyr Thr Asn Trp Asn Glu Gly Glu Pro Asn Asn Ala Gly
305                 310                 315                 320
```

```
Ser Asp Glu Asp Cys Val Leu Leu Leu Lys Asn Gly Gln Trp Asn Asp
            325                 330                335

Val Pro Cys Ser Thr Ser His Leu Ala Val Cys Glu Phe Pro Ile
            340             345                 350
```